(12) United States Patent
Enan

(10) Patent No.: US 7,541,155 B2
(45) Date of Patent: Jun. 2, 2009

(54) METHODS OF SCREENING COMPOSITIONS FOR POTENTIAL INSECT CONTROL ACTIVITY

(75) Inventor: Essam Enan, Nashville, TN (US)

(73) Assignee: Tyratech, Inc., Melbourne, FL (US)

( * ) Notice: Subject to any disclaimer, the term of this patent is extended or adjusted under 35 U.S.C. 154(b) by 519 days.

(21) Appl. No.: 10/832,022

(22) Filed: Apr. 26, 2004

(65) Prior Publication Data
US 2005/0008714 A1   Jan. 13, 2005

Related U.S. Application Data

(60) Provisional application No. 60/465,320, filed on Apr. 24, 2003, provisional application No. 60/532,503, filed on Dec. 24, 2003.

(51) Int. Cl.
*G01N 33/53* (2006.01)
*G01N 33/567* (2006.01)

(52) U.S. Cl. ...................................... 435/7.2

(58) Field of Classification Search ....................... None
See application file for complete search history.

(56) References Cited

U.S. PATENT DOCUMENTS

| | | |
|---|---|---|
| 3,943,063 A | 3/1976 | Morishita et al. |
| 3,971,852 A | 7/1976 | Brenner et al. |
| 4,211,668 A | 7/1980 | Tate |
| 4,320,113 A | 3/1982 | Kydonieus |
| 4,434,181 A | 2/1984 | Marks, Sr. et al. |
| 4,678,775 A | 7/1987 | Nathanson |
| 4,693,890 A | 9/1987 | Wilson et al. |
| 4,696,676 A | 9/1987 | Wilson et al. |
| 4,748,860 A | 6/1988 | Butler et al. |
| 4,759,228 A | 7/1988 | Butler et al. |
| 4,762,718 A | 8/1988 | Marks, Sr. |
| 4,764,367 A | 8/1988 | Wilson et al. |
| 4,783,457 A | 11/1988 | Nathanson |
| 4,801,446 A | 1/1989 | Wilson et al. |
| 4,801,448 A | 1/1989 | Wilson et al. |
| 4,808,403 A | 2/1989 | Wilson et al. |
| 4,816,248 A | 3/1989 | Wilson et al. |
| 4,818,526 A | 4/1989 | Wilson et al. |
| 4,859,463 A | 8/1989 | Wilson et al. |
| 4,876,087 A | 10/1989 | Wilson et al. |
| 4,880,625 A | 11/1989 | Wilson et al. |
| 4,885,855 A | 12/1989 | Marks, Sr. et al. |
| 4,886,662 A | 12/1989 | Wilson et al. |
| 4,892,871 A | 1/1990 | Nathanson |
| 4,902,504 A | 2/1990 | Wilson et al. |
| 4,902,690 A | 2/1990 | Nathanson |
| 4,911,906 A | 3/1990 | Wilson et al. |
| 4,943,435 A | 7/1990 | Baker et al. |
| 4,959,209 A | 9/1990 | Wilson et al. |
| 4,970,068 A | 11/1990 | Wilson et al. |
| 4,988,507 A | 1/1991 | Wilson et al. |
| 4,988,508 A | 1/1991 | Wilson et al. |
| 4,988,509 A | 1/1991 | Wilson et al. |
| 4,990,684 A | 2/1991 | Hoelderich et al. |
| 4,992,270 A | 2/1991 | Wilson et al. |
| 5,091,423 A | 2/1992 | Wilson et al. |
| 5,118,711 A | 6/1992 | Wilson et al. |
| 5,126,369 A | 6/1992 | Wilson et al. |
| 5,134,892 A | 8/1992 | Wilson et al. |
| 5,165,926 A | 11/1992 | Wilson et al. |
| 5,175,175 A | 12/1992 | Wilson et al. |
| 5,196,200 A | 3/1993 | Wilson et al. |
| 5,204,372 A | 4/1993 | Wilson et al. |
| 5,205,065 A | 4/1993 | Wilson et al. |
| 5,228,233 A | 7/1993 | Butler et al. |
| 5,250,575 A | 10/1993 | Wilson et al. |
| 5,272,179 A | 12/1993 | Butler et al. |
| 5,281,621 A | 1/1994 | Wilson et al. |
| 5,321,048 A | 6/1994 | Wilson et al. |
| 5,327,675 A | 7/1994 | Butler et al. |
| 5,344,776 A | 9/1994 | Venter et al. |
| 5,344,847 A | 9/1994 | Wilson et al. |
| 5,354,783 A | 10/1994 | Marin et al. |
| 5,366,975 A | 11/1994 | Nathanson |
| 5,387,418 A | 2/1995 | Marin et al. |
| 5,401,500 A | 3/1995 | Warren et al. |
| 5,407,609 A | 4/1995 | Tice et al. |
| 5,409,958 A | 4/1995 | Butler et al. |
| 5,417,009 A | 5/1995 | Butler et al. |

(Continued)

FOREIGN PATENT DOCUMENTS

WO    WO 98/54971 A1    12/1998

(Continued)

OTHER PUBLICATIONS

Menevse A et al. Biochem. Biophys. Res. Com. 77(2):671-677. only Abstract provided.*

(Continued)

*Primary Examiner*—Robert Landsman
(74) *Attorney, Agent, or Firm*—Davis Wright Tremaine LLP

(57) ABSTRACT

The present invention comprises compositions, methods and cell lines related to controlling insects. An embodiment of a composition comprises a plant essential oil and targets at least one receptor of insects chosen from tyramine receptor, Or83b olfactory receptor, and Or43a olfactory receptor, resulting in a change in the intracellular levels of cAMP, Ca2+, or both in the insects.

11 Claims, 14 Drawing Sheets

U.S. PATENT DOCUMENTS

| | | | |
|---|---|---|---|
| 5,418,010 A | 5/1995 | Janda et al. | |
| 5,439,690 A | 8/1995 | Knight et al. | |
| 5,439,941 A | 8/1995 | Butler et al. | |
| 5,441,988 A | 8/1995 | Butler et al. | |
| 5,447,714 A | 9/1995 | Marin et al. | |
| 5,449,695 A | 9/1995 | Marin et al. | |
| 5,458,882 A | 10/1995 | Marin et al. | |
| 5,464,626 A | 11/1995 | Warren et al. | |
| 5,472,701 A | 12/1995 | Warren et al. | |
| 5,474,898 A | 12/1995 | Venter et al. | |
| 5,521,165 A | 5/1996 | Warren et al. | |
| 5,576,010 A | 11/1996 | Warren et al. | |
| 5,576,011 A | 11/1996 | Butler et al. | |
| 5,593,600 A | 1/1997 | Solomon | |
| 5,633,236 A | 5/1997 | Warren et al. | |
| 5,635,173 A | 6/1997 | Warren et al. | |
| 5,635,174 A | 6/1997 | Warren et al. | |
| 5,665,781 A | 9/1997 | Warren et al. | |
| 5,683,687 A | 11/1997 | Marin et al. | |
| 5,693,344 A | 12/1997 | Knight et al. | |
| 5,703,104 A | 12/1997 | Peck et al. | |
| 5,753,686 A | 5/1998 | Marin et al. | |
| 5,772,983 A | 6/1998 | O'Connell et al. | |
| 5,785,982 A | 7/1998 | Warren et al. | |
| 5,814,325 A | 9/1998 | Rod | |
| 5,840,669 A | 11/1998 | Neelakantan | |
| 5,855,903 A | 1/1999 | Warren et al. | |
| 5,980,931 A | 11/1999 | Fowler et al. | |
| 5,990,178 A | 11/1999 | Ninkov | |
| 5,998,484 A | 12/1999 | Zobitne et al. | |
| 6,004,569 A | 12/1999 | Bessette et al. | |
| 6,006,470 A | 12/1999 | Geoghegan et al. | |
| 6,024,874 A | 2/2000 | Lott | |
| 6,114,384 A | 9/2000 | Bessette et al. | |
| 6,143,288 A | 11/2000 | Warren et al. | |
| 6,183,767 B1 | 2/2001 | Bessette et al. | |
| 6,255,356 B1 | 7/2001 | Butler | |
| 6,272,790 B1 | 8/2001 | Paganessi et al. | |
| 6,322,825 B1 | 11/2001 | Ninkov | |
| 6,329,433 B1 | 12/2001 | Bessette et al. | |
| 6,331,572 B1 | 12/2001 | Bessette et al. | |
| 6,333,302 B1 | 12/2001 | Beer et al. | |
| 6,333,360 B1 | 12/2001 | Bessette et al. | |
| 6,340,710 B1 | 1/2002 | Bessette et al. | |
| 6,342,535 B1 | 1/2002 | Bessette et al. | |
| 6,342,536 B1 | 1/2002 | Bessette et al. | |
| 6,360,477 B1 | 3/2002 | Flashinski et al. | |
| 6,368,508 B1 | 4/2002 | Gatz et al. | |
| 6,372,801 B1 | 4/2002 | Bessette et al. | |
| 6,372,803 B1 | 4/2002 | Bessette et al. | |
| 6,376,556 B1 | 4/2002 | Bessette et al. | |
| 6,395,789 B1 | 5/2002 | Bessette et al. | |
| 6,414,036 B1 | 7/2002 | Ninkov | |
| 6,451,844 B1 | 9/2002 | Watkins et al. | |
| 6,506,707 B1 | 1/2003 | Bessette | |
| 6,531,163 B1 | 3/2003 | Bessette et al. | |
| 6,534,099 B1 | 3/2003 | Bessette et al. | |
| 6,548,085 B1 | 4/2003 | Zobitne et al. | |
| 6,555,121 B1 | 4/2003 | Bessette et al. | |
| 6,610,254 B1 | 8/2003 | Furner et al. | |
| 6,649,660 B2 | 11/2003 | Ninkov | |
| 6,660,288 B1 | 12/2003 | Behan et al. | |
| 6,670,311 B1 | 12/2003 | Aldcroft et al. | |
| 6,689,395 B2 | 2/2004 | Bessette | |
| 6,713,518 B1 | 3/2004 | Bessette et al. | |
| 6,812,258 B2 | 11/2004 | Bessette et al. | |
| 6,841,577 B2 | 1/2005 | Bessette et al. | |
| 6,844,369 B2 | 1/2005 | Ninkov | |
| 6,849,614 B1 | 2/2005 | Bessette et al. | |
| 6,858,653 B1 | 2/2005 | Bessette | |
| 6,887,899 B1 | 5/2005 | Bessette | |
| 6,921,539 B2 | 7/2005 | Ninkov | |
| 6,949,587 B1 | 9/2005 | Bessette | |
| 6,969,522 B2 | 11/2005 | Bessette | |
| 6,974,584 B2 | 12/2005 | Bessette | |
| 6,986,898 B1 | 1/2006 | Bessette | |
| 7,008,649 B2 | 3/2006 | Bessette et al. | |
| 7,109,240 B2 | 9/2006 | Bessette et al. | |
| 7,201,926 B2 | 4/2007 | Fried et al. | |
| 7,208,519 B2 | 4/2007 | Ninkov | |
| 7,238,726 B2 | 7/2007 | Bessette | |
| 7,238,798 B2 * | 7/2007 | Lee et al. | 536/23.5 |
| 7,241,806 B2 | 7/2007 | Bessette | |
| 7,250,175 B2 | 7/2007 | Bessette et al. | |
| 7,291,650 B2 | 11/2007 | Bessette et al. | |
| 7,320,966 B2 | 1/2008 | Bessette et al. | |
| 7,351,420 B2 | 4/2008 | Bessette et al. | |
| 7,357,939 B2 | 4/2008 | Bessette | |
| 7,361,366 B2 | 4/2008 | Bessette et al. | |
| 7,381,431 B2 | 6/2008 | Baker et al. | |
| 2002/0028256 A1 | 3/2002 | Bessette | |
| 2002/0034556 A1 | 3/2002 | Khazan | |
| 2002/0073928 A1 | 6/2002 | Ingman et al. | |
| 2002/0076360 A1 | 6/2002 | Ingman et al. | |
| 2002/0081230 A1 | 6/2002 | Ingman et al. | |
| 2002/0096121 A1 | 7/2002 | Ingman et al. | |
| 2002/0107287 A1 | 8/2002 | Bessette et al. | |
| 2003/0026823 A1 | 2/2003 | Fried et al. | |
| 2003/0036530 A1 | 2/2003 | Bessette | |
| 2003/0039674 A1 | 2/2003 | Bessette | |
| 2003/0091657 A1 | 5/2003 | Chiasson | |
| 2003/0091661 A1 | 5/2003 | Bessette | |
| 2003/0108622 A1 | 6/2003 | Bessette et al. | |
| 2003/0108623 A1 | 6/2003 | Bessette et al. | |
| 2003/0175369 A1 | 9/2003 | Khazan-Enache | |
| 2003/0194454 A1 | 10/2003 | Bessette et al. | |
| 2004/0146595 A1 | 7/2004 | Bessette et al. | |
| 2004/0156922 A1 | 8/2004 | Bessette et al. | |
| 2004/0185080 A1 | 9/2004 | Hojo et al. | |
| 2004/0192551 A1 | 9/2004 | Bessette | |
| 2004/0213822 A1 | 10/2004 | Birch et al. | |
| 2004/0248791 A1 | 12/2004 | Spana et al. | |
| 2005/0004233 A1 | 1/2005 | Bessette et al. | |
| 2005/0008714 A1 | 1/2005 | Enan | |
| 2005/0013885 A1 | 1/2005 | Chiasson | |
| 2005/0019269 A1 | 1/2005 | Marks et al. | |
| 2005/0070576 A1 | 3/2005 | Spooner-Hart et al. | |
| 2005/0136089 A1 | 6/2005 | Bessette et al. | |
| 2005/0143260 A1 | 6/2005 | Bessette et al. | |
| 2005/0147636 A1 | 7/2005 | Bessette et al. | |
| 2005/0163869 A1 | 7/2005 | Bessette et al. | |
| 2005/0170024 A1 | 8/2005 | Bessette et al. | |
| 2005/0170025 A1 | 8/2005 | Bessette et al. | |
| 2005/0170026 A1 | 8/2005 | Bessette et al. | |
| 2005/0214267 A1 | 9/2005 | Enan | |
| 2005/0260241 A1 | 11/2005 | Bessette et al. | |
| 2005/0260242 A1 | 11/2005 | Bessette et al. | |
| 2005/0288227 A1 | 12/2005 | Marks et al. | |
| 2006/0088564 A1 | 4/2006 | Bessette | |
| 2006/0115507 A1 | 6/2006 | Bessette | |
| 2006/0115508 A1 | 6/2006 | Bessette | |
| 2006/0115509 A1 | 6/2006 | Bessette | |
| 2006/0115510 A1 | 6/2006 | Bessette | |
| 2006/0121074 A1 | 6/2006 | Bessette | |
| 2007/0098750 A1 | 5/2007 | Bessette | |
| 2007/0178128 A1 | 8/2007 | Bessette | |
| 2007/0190094 A1 | 8/2007 | Bessette | |
| 2007/0207221 A1 | 9/2007 | Bessette et al. | |
| 2007/0298131 A1 | 12/2007 | Bessette et al. | |
| 2007/0299037 A1 | 12/2007 | Bessette et al. | |
| 2007/0299038 A1 | 12/2007 | Bessette et al. | |
| 2008/0003315 A1 | 1/2008 | Bessette et al. | |
| 2008/0003316 A1 | 1/2008 | Bessette et al. | |
| 2008/0003317 A1 | 1/2008 | Bessette et al. | |

| | | | |
|---|---|---|---|
| 2008/0004240 A1 | 1/2008 | Bessette et al. | |
| 2008/0015167 A1 | 1/2008 | Bessette et al. | |
| 2008/0015249 A1 | 1/2008 | Bessette et al. | |
| 2008/0020381 A1 | 1/2008 | Henrich et al. | |
| 2008/0032387 A1 | 2/2008 | Bailey et al. | |
| 2008/0038383 A1 | 2/2008 | Bessette et al. | |
| 2008/0153904 A1 | 6/2008 | Bessette et al. | |

FOREIGN PATENT DOCUMENTS

| | | |
|---|---|---|
| WO | WO 99/21891 A1 | 5/1999 |
| WO | WO 99/33973 A2 | 7/1999 |
| WO | WO 99/33973 A3 | 7/1999 |
| WO | WO 00/05964 A1 | 2/2000 |
| WO | WO 00/21364 A2 | 4/2000 |
| WO | WO 0050566 A2 * | 8/2000 |
| WO | WO 00/51436 A1 | 9/2000 |
| WO | WO 00/53020 A1 | 9/2000 |
| WO | WO 00/75322 A1 | 12/2000 |
| WO | WO 00/00020 A1 | 1/2001 |
| WO | WO 01/00026 A1 | 1/2001 |
| WO | WO 01/00032 A1 | 1/2001 |
| WO | WO 01/00033 A1 | 1/2001 |
| WO | WO 01/00034 A1 | 1/2001 |
| WO | WO 01/00049 A1 | 1/2001 |
| WO | WO 01/10214 A2 | 2/2001 |
| WO | WO 01/10214 A3 | 2/2001 |
| WO | WO 01/18201 A1 | 3/2001 |
| WO | WO 01/60163 A2 | 8/2001 |
| WO | WO 01/60163 A3 | 8/2001 |
| WO | WO 01/91554 A1 | 12/2001 |
| WO | WO 01/91556 A2 | 12/2001 |
| WO | WO 01/91556 A3 | 12/2001 |
| WO | WO 01/91560 A2 | 12/2001 |
| WO | WO 01/91560 A3 | 12/2001 |
| WO | WO 03/016477 A2 | 2/2003 |
| WO | WO 03/016477 A3 | 2/2003 |
| WO | WO 2004/006968 A1 | 1/2004 |
| WO | WO 2004/100971 A1 | 11/2004 |
| WO | WO 2005/092016 A2 | 10/2005 |
| WO | WO 2005/092016 A3 | 10/2005 |

OTHER PUBLICATIONS

Bischof, et al.; *Cloning expression and functional analysis of an octopamine receptor from Periplaneta Americana*; Insect Biochem Mol Biol; 34:6:511-521, Jun. 2004.

Coats, et al.; *Toxicity and neurotoxic effects of monoterpenoids in insects and earthworms*; ACS publication; 1991.

Enan, Essam, et al.; *Insectidical action of terpenes and phenols to cockroaches: effect on octopamine receptors*; International Symposium on Crop Protection, Ghent, Belgium; May 1998.

Enan, Essam, et al.; *Insecticidal activity of essential oils: octopaminergic sites of action*; Comp. Biochem. Physiol. C Toxicol.; 130:325-337; 2001.

Evans, et al.; *Agonist-specific coupling of G-protein-coupled receptors to second-messenger systems*; Progress in Brain Research; vol. 106; 1999; 259-268.

Kutsukake, Mayako, et al; *A tyramine receptor gene mutation causes a defective olfactory behavior in Drosophila*; Gene; Mar. 7, 2000; 245:1; 31-42.

Muller-Riebau, et al.; *Chemical Composition and Fungitoxic Properties to Phytopathogenic Fungi of Essential Oils of Selected Aromatic Plant Growing Wild in Turkey*; J Agric. Food chem.; 43: 2262-2266; 1995.

Rice, et al.; *Insecticidal properties of monoterpenoid derivatives to the house fly (diptera: muscidae) and red flour beetle (coleoptera: tenebrionidae)*; Pesticide Science; vol. 44; 1994; 195-202.

Rice, et al.; *Bioregulators for Crop Protection and Pest Control*, Chapter Structural requirements for Monoterpenoid Activity Against Insects; American Chemical Society Symposium Series developed from a symposium sponsored by the Division of Agrochemicals at the 205th National Meeting of the American Chemical Society in Denver, Colorado, Mar. 28-Apr. 2, 1993.

Robb, S., et al.; *Agonist-specific coupling of a cloned Drosophila octopamine/tyramine receptor to multiple second messenger systems*; EMBO J.; Mar. 15, 1994; 13:6; 1325-1330.

Saudou, F., et al.; *Cloning and characterization of a Drosophila tyramine receptor*; EMBO J.; Nov. 1990; 9:11; 3611-3617.

Tsao, et al.; *Monoterpenoids and their synthetic derivatives as leads for new insect-control agents*; American Chemical Society; Chapter 28; 1995.

Von Nickisch-Rosenegk, et al.; *Cloning of biogenic amine receptors from moths (Bombyx mori and Heliothis virescens)*; Insect Biochem Mol Biol; Sep.-Oct. 1996; 26:8-9; 817-827.

Notification of Transmittal of the International Search Report and the Written Opinion of the International Searching Authority, or the Declaration; International Search Report; Written Opinion of the International Searching Authority (mailed Nov. 5, 2004), 7 pages in International Application No. PCT/US04/12947.

Abou El Ele, Nadia E. and Enan, Essam E., *Bulletin of High Institute of Public Health*, University of Alexandria, Alexandria, Egypt, 31(1):15-30, Jan. 2001. Insecticidal Activity of Some Essential Oils: cAMP Mediates Effect.

Alvarez-Sanchez, Maria Elizabeth et al., *Microbial Pathogenesis*, 28(4):193-202, Apr. 2000. "A novel cysteine proteinase (CP65) of *Trichomonas vaginalis* involved in cytotoxicity".

Aoyama, Masato et al., *Archives of Insect Biochemistry and Physiology*, 47(1):1-7, May 2001. "Substituent-dependent, Positive and Negative Modulation of *Bombyx mori* Adenylate Cyclase by Synthetic Octopamine-Tyramine Analogues".

Arakawa, Shoji et al., *Neuron*, 4(3):343-354, Mar. 1990. "Cloning, Localization, and Permanent Expression of a *Drosophila* Octapamine Receptor".

Baxter, Glenn D. et al., *Insect Biochemistry and Molecular Biology*, 29(5):461-467, May 1999. "Isolation of a cDNA for an octopamine-like, G-protein coupled receptor from the cattle tick, *Boophilus microplus*".

Berntzen Allen K. et al., The Journal of Parisitology, 51(2):235-242, Apr. 1965. "In vitro Hatching of Oncospheres of Four Hymenolepidid Cestodes".

Blenau, Wolfgang et al., *Journal of Neurochemistry*, 74(3): 900-908, Mar. 2000. Amtyr1: Characterization of a Gene from Honeybee (*Apis mellifera*) Brain Encoding a Functional Tyramine Receptor.

Blenau, Wolfgang et al., *Archives of Insect Biochemistry and Physiology*, 48(1):13-38, Sep. 2001. "Molecular and Pharmacological Properties of Insect Biogenic Amine Receptors: Lessons From *Drosophila melanogastor* and *Apis mellifera*".

Borowsky, Beth et al., *Proc. Natl. Acad. Sci. USA*, 98(16):8966-8971, Jul. 31, 2001. "Trace amines: Identification of a family of mammalian G protein-coupled receptors".

Bunzow, James R. et al., *Molecular Pharmacology*, 60(6):1181-1188, Dec. 2001. "Amphetamine, 3,4-Methylenedioxymethamphetamine, Lysergic Acid Diethylamide, and Metabolites of the Catecholamine Neurotransmitters Are Agonists of a Rat Trace Amine Receptor".

Chirgwin, John M. et al., *Biochemistry*, 18(24):5294-5299, Nov. 27, 1979. "Isolation of Biologically Active Ribonucleic Acid from Sources Enriched Ribonuclease".

Coats, Joel R., *Environmental Health Perspectives*, 87:255-262, 1990. "Mechanisms of Toxic Action and Structure-Activity Relationships for Organochlorine and Synthetic Pyrethroid Insecticides".

Colby, S.R., *Weeds*, 15:(1):20-22, 1967. "Calculating synergistic and Antagonistic Responses of Herbicide Combinations".

Cooley, Lynn et al., *Science*, 239(4844):1121-1128, Mar. 4, 1988. "Insertional Mutagenesis of the *Drosophila* Genome with Single P Elements".

Donini, Andrew et al., Journal of Insect Physiology 50(4):351-361, Apr. 2004. "Evidence for a possible neurotransmitter-neuromodulator role of tyramine on the locust oviducts".

Downer, R.G.H. et al., *Neurochemical Research* 18(12):1245-1248; Dec. 1993. "Characterization of the Tyraminergic System in the Central Nervous System of the Locust, *Locusta migratoria migratoides*".

Downer, Roger G.H. et al., "Biogenic Amines in Insects", in *Insect Neurochemistry and Neurophysiology 1993* (Borkovec A.B. and Loeb M.J., eds), pp. 23-38. CRC Press, Boca Raton, Florida, 1994.

Dudai, Yadin et al., *Journal of Neurochemistry* 38(6):1551-1558, Jun. 1982. "Aminergic Receptors in *Drosophila melanogaster*: Properties of [$^3$H]Dihydroergocryptine Binding Sites".

Enan, Essam et al., *Biochemical Pharmacology*, 51(4):447-454, Feb. 23, 1996. "Deltamethrin-Induced Thymus Atrophy in Male Balb-c Mice".

Evans, Peter D., *Journal of Physiology*, 318:99-122, Sep. 1981. "Multiple receptor types for octopamine in the locust".

Evans, Peter D. et al., *Nature*, 287(5777):60-62, Sep. 4, 1980. "Action of formamidine pesticides on octopamine receptors".

Finney, D.J., *Probit Analysis*, 3rd Ed., pp. 33-37, Cambridge University Press, London, 1971.

Gerhardt, Cindy C. et al., *Molecular Pharmacology*, 51(2):293-300, Feb. 1997. "Molecular Cloning and Pharmacological Characterization of a Molluscan Octopamine Receptor".

Grodnitsky, Justin A. et al., *Journal of Agricultural and Food Chemistry*, 50(16):4576-4580, Jul. 31, 2002. "QSAR Evaluation of Monoterpenoids' Insecticidal Activity".

Grundy, Dawn L. & Still, *Pesticide Biochemistry and Physiology*, 23(3):383-388, 1985. "Inhibition of Acetylcholinesterases by Pulegone- 1,2-epoxide".

Gudermann, Thomas et al., *Annu. Rev. Pharmacol. Toxicol.*, 36:429-459, Apr. 1996. "Diversity and selectivity of receptor-G protein interaction".

Gudermann, Thomas et al., *Annual Review Neuroscience*, 20:399-427; Mar. 1997. "Functional and structural complexity of signal transduction via G-protein-coupled receptors".

Guillén, A. et al., *Life Sciences*, 45(7):655-662, 1989. "A possible new class of octopamine receptors coupled to adenylate cyclase in the brain of the dipterous *Ceratitis capitata*. Pharmacological characterization and regulation of $^3$H-octopamine binding".

Han, Kyung-An et al., *Journal of Neuroscience*, 18(10):3650-3658, May 15, 1998. "A Novel Octopamine Receptor with Preferential Expression in Drosophila Mushroom Bodies".

Hori, Masatoshi, *Applied Entomology and Zoology*, 34(3):351-358, 1999. "The effects of rosemary and ginger oils on the alighting behavior of *Myzus persicae* (Sulzer) (*Homoptera: Aphididae*) and on the incidence of yellow spotted streak".

Ito, Akira, *Parasitology*, 71(3):465-473, Dec. 1975. "In vitro oncospheral agglutination given by immune sera from mice infected, and rabits injected, with eggs of *Hymenolepis nana*".

Karr, L.L. et al., *Journal of Economic Entomology*, 85(2):424-429, Apr. 1992. "Effects of Four Monoterpenoids on Growth and Reproduction of the German Cockroach (*Blattodea: Blattellidae*)".

Khan, Md. Anwar Arfien, et al., *Archives of Insect Biochemistry and Physiology*, 52(1):7-16, Jan. 2003, (EPub: Dec. 17, 2002). "Positive and Negative Modulation of Bombyx mori Adenylate Cyclase by 5-Phenyloxazoles: Identification of Octopamine and Tyramine Receptor Agonists".

Kostyukovsky, Moshe et al., *Pest Management Science*, 58(11):1101-1106, Sep. 30, 2002. "Activation of octopaminergic receptors by essential oil constituents isolated from aromatic plants: possible mode of action against insect pests".

Kravitz, Edward A. et al., *Neuroscience Symposia*, 1:67-81, 1976. "Octopamine Neurons in Lobsters".

Kyte, Jack et al., *Journal of Molecular Biology*, 157(1):105-132, May 5, 1982. (Abstract Only) "A simple method for displaying the hydropathic character of a protein".

Landolt, Peter J. et al., *Environmental Entomology*, 28(6):954-960, Dec. 1999. Plant Essential oils as Arrestants and Repellents for Neonate Larvae of the Coding Moth (*Lepidoptera: tortricidae*).

Lee, Sangkyun et al., *Journal of Economic Entomology*, 90(4):883-892, Aug. 1997. "Insecticidal Activity of monoterpenoids to Western Corn Rootworm (*Coleoptera: chrysomelidae*), Twospotted Spider Mite (*Acari: tetranychidae*), and House Fly (*Diptera: muscidae*)".

Lomasney, Jon W. et al., *Proc. Natl. Acad. Sci. USA*, 87(13):5094-5098, Jul. 1990. "Expansion of the $\alpha_2$-adrenergic receptor family: Cloning and characterization of a human $\alpha_2$-adrenergic receptor subtype, the gene for which is located on chromosome 2".

Lynn, Dwight E., *Cytotechnology*, 20(2):3-11, Apr. 11, 1996. "Development And Characterization Of Insect Cell Lines".

Lynn, Dwight E., *Journal of Insect Science*, 2:9 (6 pages), published online May 20, 2002 "Methods for Maintaining Insect Cell Cultures".

Michon, Pascal, et al., *Molecular Biology and Evolution*, 19(7):1128-1142, Jul. 2002. "Evolutionary Relationships of Conserved Cysteine-Rich Motifs in Adhesive Molecules of Malaria Parasites".

Miyazawa, Mitsuo et al., *J. Agric. Food Chem.*, 45(3):677-679, Mar. 1997. "Inhibition of Acetylcholinesterase Activity by Monoterpenoids with a *p*-Menthane Skeleton".

Morty, Rory E., *Journal of Biological Chemistry*, 274(37):26149-26156, Sep. 10, 1999. "Oligopeptidase B from *Trypanosoma brucei*, a New Member of an Emerging Subgroup of Serine Oligopeptidases".

Ngoh, Shay P. et al., *Pesticide Science*, 54(3):261-268, 1998. "Insecticidal and Repellent Properties of Nine Volatile Constituents of Essential Oils against the American Cockroach, *Periplaneta americana* (L.)".

Nok, Andrew J. & Rivera, Windell, *Parasitology Research*, 89(4):302-307, Mar. 2003, (Epub: Nov. 14, 2002). "Characterization of sialidase from *Entamoaeba hystolitica* and possible pathogenic role in amebiasis".

Ohta, H. et al., *Insect Molecular Biology*, 12(3):217-223, Jun. 2003. "B69Bom encodes a *Bombyx mori* tyramine receptor negatively coupled to adenylate cyclase".

Orchard, Ian, *Canadian Journal of Zoology*, 60:659-669, 1982. "Octopamine in insects: neruotransmitter, neurohormone, and neuromodulator".

Pearson, Richard D. et al., *Annals of Internal Medicine*, 99(2):195-198, Aug. 1983. "Praziquantel: A Major Advance in Anthelminthic Therapy".

Rex, Elizabeth et al., *Journal of Neurochemistry*, 82(6):1352-1359, Sep. 2002. "Characterization of a tyramine receptor from *Caenorhabditis elegans*".

Robertson, H.A. et al., *Int. Rev. Neurobiol.*, 19:173-224, 1976. "Octopamine and some related noncatecholic amines in invertebrate nervous systems".

Roeder, T. *Life Science*, 50(1): 21-28, 1992. "A new octopamine receptor class in locust nervous tissue, the octopamine 3 (OA3) receptor".

Roeder, T., *Comparative Biochemistry Physiology*, Part C, 107(1):1-12, 1994. "Biogenic amines and their receptors in insects".

Roeder, T., *Progress in Neurobiology*, 59(5):533-561, Dec. 1999. "Octopamine in Invertebrates".

Ryan, M.F. et al., *Journal of Chemical Ecology*, 14(10);1965-1975, Oct. 1988. Plant-insect coevolution and inhibition of acetylcholinesterase.

Sangwan, Naresh K. et al., *Pesticide Science*, 28(3):331-335, 1990. "Nematicidal Activity of Some Essential Plant Oils".

Sawamura, Masayoshi et al, *Journal of Agricultural Food Chemistry*, 47(12):4868-4872, Nov. 9, 1999. "Inhibitory Effects of Citrus Essential Oils and Their Components on the Formation of *N*-Nitrosodimethylamine".

Shulaev, Vladimir et al., *Nature*, 385:718-721, Feb. 20, 1997. "Airborne signalling by methyl salicylate in plant pathogen resistance".

Urban, Martin, et al., *EMBO Journal*, 18(3):512-521, Feb. 1, 1999. "An ATP-driven efflux pump is a novel pathogenicity factor in rice blast disease".

Van Poyer, Wendy et al., *Insect Biochemistry and Molecular Biology*, 31(4-5):333-338, Mar. 15, 2001. "Phenolamine-dependent adenylyl cyclase activation in *Drosophila schneider* 2 cells".

Vanden Broeck, J. et al., *Journal of Neurochemistry*, 64(6):2387-2395, Jun. 1995. "Characterization of a Cloned Locust Tyramine Receptor cDNA by Functional Expression in Permanently Transformed Drosophila S2 Cells".

Verner, Philippe et al., *Trends in Pharmacological Sciences*, 16(11):375-381, Nov. 1995. "An evolutionary view of drug-receptor interaction: the bioamine receptor family".

Yu, J-R. et al., *Parasitology Research*, 88(5):412-420, May 2002, (Epub: Feb. 6, 2002). "A common oocyst surface antigen of *Cryptosporidium* recognized by monoclonal antibodies".

\* cited by examiner

US 7,541,155 B2

METHODS OF SCREENING COMPOSITIONS FOR POTENTIAL INSECT CONTROL ACTIVITY

CROSS REFERENCES TO RELATED APPLICATION

This application claims priority to U.S. Provisional Application Ser. No. 60/465,320 filed Apr. 24, 2003 and U.S. Provisional Application Ser. No. 60/532,503 filed Dec. 24, 2003, which are both incorporated herein in their entirety by this reference.

FIELD OF THE INVENTION

The present invention relates to compositions, methods, cell lines and reports related to controlling insects.

BACKGROUND OF THE INVENTION

Animals have chemosensory and mechanosensory systems that recognize a large array of environmental stimuli, generating behavioral responses. Behavioral studies have been conducted to understand the genetics of these systems. The olfactory system plays a role in the survival and maintenance of species, including insects.

Drosophila is one of the models for studying the sensory system, as it is amenable to mutant analysis using molecular techniques, behavioral analysis, and electrophysiological analysis, and because its olfactory system is comparable to the mammalian counterpart.

Various chemicals and mixtures have been studied for pesticidal activity for many years with a goal of obtaining a product which is selective for invertebrates such as insects and has little or no toxicity to vertebrates such as mammals, fish, fowl and other species and does not otherwise persist in and damage the environment.

Most of the previously known and commercialized products having sufficient pesticidal activity to be useful also have toxic or deleterious effects on mammals, fish, fowl or other species which are not the target of the product. For example, organophosphorus compounds and carbamates inhibit the activity of acetylcholinesterase in insects as well as in all classes of animals. Chlordimeform and related formamidines are known to act on octopamine receptors of insects but have been removed from the market because of cardiotoxic potential in vertebrates and carcinogenicity in animals and a varied effect on different insects. Other compounds, which may be less toxic to mammals and other non-target species, are sometimes difficult to identify.

SUMMARY OF THE INVENTION

The present invention comprises compositions for controlling insects and methods for using these compositions. The present invention comprises compositions for controlling insects, which comprise one or more plant essential oils and methods for using these compositions. The plant essential oils, when combined, may have a synergistic effect. The compositions may include a fixed oil, which is a non-volatile non-scented plant oil. Additionally, it is contemplated that these compositions may be made up of generally regarded as safe (GRAS) compounds.

The present invention comprises compositions comprising one or more plant essential oils and an insect control agent, and methods for using these compositions. Examples of insect control agent include, DEET and D-allethrin. The plant essential oil and the insect control agent, when combined, may have a synergistic effect. For example, the insect control activity of 29% DEET may be achieved with 5% DEET when included in a combination of the present invention.

The present invention comprises a method for screening compositions for insect control activity. The present invention comprises cell lines stably transfected with tyramine receptor (TyrR), Or83b Olfactory Receptor (Or83b), or Or43a Olfactory Receptor, which may be used to screen compositions for insect control activity.

The present invention comprises a method for generating a report identifying one or more compositions having insect control activity. The term "report" refers to statements or descriptions contained in a printed document, a database, a computer system, or other medium.

For purposes of simplicity, the term "insect" shall be used through out this application; however, it should be understood that the term "insect" refers, not only to insects, but also to arachnids, larvae, and like invertebrates. Also for purposes of this application, the term "insect control" shall refer to having a repellant effect, a pesticidal effect, or both. "Repellant effect" is an effect, wherein more insects are repelled away from a host or area that has been treated with the composition than a control host or area that has not been treated with the composition. In some embodiments, repellant effect is an effect wherein at least about 75% of insects are repelled away from a host or area that has been treated with the composition. In some embodiments, repellant effect is an effect wherein at least about 90% of insects are repelled away from a host or area that has been treated with the composition. "Pesticidal effect" is an effect, wherein treatment with a composition causes at least about 1% of the insects to die. In this regard, an LC1 to LC100 (lethal concentration) or an LD1 to LD100 (lethal dose) of a composition will cause a pesticidal effect. In some embodiments, the pesticidal effect is an effect, wherein treatment with a composition causes at least about 5% of the exposed insects to die. In some embodiments, the pesticidal effect is an effect, wherein treatment with a composition causes at least about 10% of the exposed insects to die. In some embodiments, the pesticidal effect is an effect, wherein treatment with a composition causes at least about 25% of the insects to die. In some embodiments the pesticidal effect is an effect, wherein treatment with a composition causes at least about 50% of the exposed insects to die. In some embodiments the pesticidal effect is an effect, wherein treatment with a composition causes at least about 75% of the exposed insects to die. In some embodiments the pesticidal effect is an effect, wherein treatment with a composition causes at least about 90% of the exposed insects to die. In some embodiments of the invention, treatment with such concentrations or doses will result in a knockdown of the insects occurring within a few seconds to a few minutes.

The compositions of the present invention may be used to control insects by either treating a host directly, or treating an area in which the host will be located, for example, an indoor living space, outdoor patio or garden. For purposes of this application, host is defined as a plant, human or other animal.

DETAILED DESCRIPTION OF THE INVENTION

Figure 1:
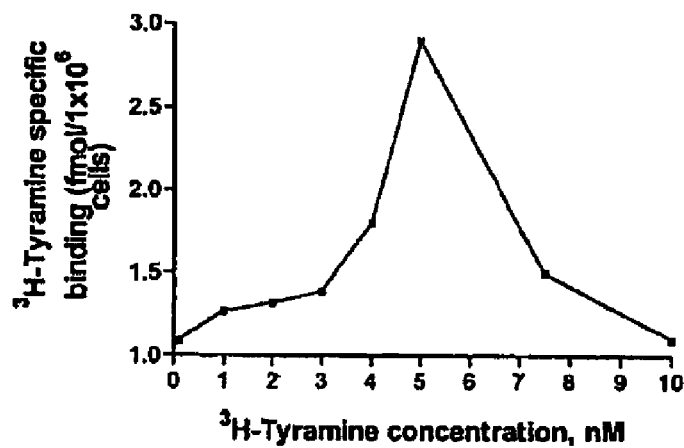
FIG. 1 shows the receptor-specific binding in Schneider cells transfected with the tyramine receptor.

The present invention relates to compositions, methods, cell lines and reports related to controlling insects. The insect control may be related to one or more of the receptors, comprising tyramine receptor (TyrR), Or83b Olfactory receptor (Or83b), and Or43a olfactory receptor (Or43a).

The present invention comprises a method for screening compositions for insect control activity. The present invention comprises Drosophila Schneider cell lines stably transfected with TyrR, Or43a, or Or83b, which may be used to screen compositions for insect control activity. The nucleic acid sequence and the peptide sequence of TyrR are set forth in SEQ ID NO: 1 and SEQ ID NO: 2, respectively. The nucleic acid sequence and the peptide sequence of Or43a are set forth in SEQ ID NO: 3 and SEQ ID NO: 4, respectively. The nucleic acid sequence and the peptide sequence of Or83b are set forth in SEQ ID NO: 5 and SEQ ID NO: 6, respectively.

The potential for insect control activity may be identified by measuring the affinity of the test compositions for the receptor in the cell lines expressing TyrR, Or83b, and/or Or43a. The potential for insect control activity may also be identified by measuring the change in intracellular cAMP and/or $Ca^{2+}$ in the cell lines expressing TyrR, Or83b, and/or Or43a following treatment with the test compositions. The gene sequences of the TyrR receptor, the Or 83b receptor and the Or 43a receptor have substantial similarity between various insect species. As such, the *Drosophila Schneider* cell lines expressing these receptors may be used to screen for compositions having insect control activity in various insect species.

The present invention comprises compositions for controlling insects and methods for using these compositions. The present invention comprises compositions for controlling insects, which comprise one or more plant essential oils and methods for using these compositions. The plant essential oils, when combined, may have a synergistic effect. The compositions of the present invention may include any of the following oils, or mixtures thereof:

t-anthole
Black seed oil (BSO)
camphene
carvacrol
d-carvone
l-carvone
1,8-cineole
p-cymene
diethyl phthalate
eugenol
geraniol
isopropyl citrate
lemon grass oil
lilac flower oil (LFO)
lime oil
d-limonene
linalyl anthranilate
linalool
lindenol
methyl citrate
methyl di-hydrojasmonate
myrcene
perillyl alcohol
phenyl acetaldehyde
α-pinene
β-pinene
piperonal
piperonyl
piperonyl acetate
piperonyl alcohol
piperonyl amine
quinone
sabinene
α-terpinene
terpinene 900
α-terpineol
gamma-terpineol
2-tert-butyl-p-quinone
α-thujone
thyme oil
thymol The compositions of the present invention may also include any of the following oils, or mixtures thereof:

Allyl sulfide
Allyl trisulfide
Allyl-disulfide
Anethole
Artemisia alcohol acetate
Benzyl acetate
Benzyl alcohol
Bergamotene
β-bisabolene
Bisabolene oxide -continued α-bisabolol
Bisabolol oxide
Bisobolol oxide β
Bornyl acetate
β-bourbonene
α-cadinol
Camphene
α-campholene
α-campholene aldehyde
camphor
Caryophyllene oxide
Chamazulene
Cinnamaldehyde
Cis-verbenol
Citral A
Citral B
Citronellal
Citronellol
Citronellyl acetate
Citronellyl formate
α-copaene
cornmint oil
β-costol
Cryptone
Curzerenone
d-Carvone
l-Carvone
Davanone
Diallyl tetrasulfide
dihydropyrocurzerenone
β-elemene
gamma-elemene
Elmol
Estragole
2-ethyl-2-hexen-1-ol
Eugenol acetate
α-farnesene
(Z,E)-α-farnesene
E-β-farnesene
Fenchone
Furanodiene Furanoeudesma-1,3-diene
Furanoeudesma-1,4-diene
Furano germacra 1,10(15)-diene-6-one
Furanosesquiterpene
Geraniol
Geraniol acetate
Germacrene D
Germacrene B
α-gurjunene
α-humulene
α-ionone
β-ionone
Isoborneol
Isofuranogermacrene
Iso-menthone
Iso-pulegone
Jasmone
Lilac flower oil
Limonene
Linalool
Linalyl acetate
Lindestrene
Methyl-allyl-trisulfide
Menthol
2-methoxy furanodiene
menthone
Menthyl acetate
Methyl cinnamate
Menthyl salicylate
Myrtenal
Neraldimethyl acetate
Nerolidol
Nonanone
1-octanol
E ocimenone
Z ocimenone
3-octanone
Ocimene
Octyl acetate -continued Peppermint oil
α-phellandrene
β-phellandrene
piperonal
Prenal
Pulegone
Sabinene
Sabinyl acetate
α-santalene
Santalol
Sativen
δ-selinene
β-sesquphelandrene
Spathulenol
Tagetone
α-terpinene
4-terpineol
α-terpinolene
α-terpinyl acetate
α-thujene
Thymyl methyl ether
Trans-caryophyllene
Trans-pinocarveol
Trans-verbenol
Verbenone
Yomogi alcohol
Zingiberene
Dihydrotagentone In those compositions including more than one oil, each oil may make up between about 1% to about 99%, by weight, of the composition mixture. For example, one composition of the present invention comprise about 1% thymol and about 99% geraniol. Optionally, the compositions may additionally comprise a fixed oil, which is a non-volitile non-scented plant oil. For example, the composition could include one or more of the following fixed oils:

castor oil
corn oil
cumin oil
mineral oil
olive oil
peanut oil
safflower oil
sesame oil
soy bean oil For example, one composition of the present invention includes about 1% thymol, about 50% geraniol and about 49% mineral oil. Additionally, it is contemplated that these compositions may be made up of generally regarded as safe (GRAS) compounds, for example: thyme oil, geraniol, lemon grass oil, lilac flower oil, black seed oil, lime oil, eugenol, castor oil, mineral oil, and safflower oil.

The present invention comprises compositions comprising one or more plant essential oils and an insect control agent, for example, DEET, and D-allethrin, and methods for using these compositions. The plant essential oil and the insect control agent, when combined, may have a synergistic effect. For example, the insect control activity of 29% DEET may be achieved with 5% DEET when included in a combination of the present invention.

The compositions of the present invention may comprise, in admixture with a suitable carrier and optionally with a suitable surface active agent, two or more plant essential oil compounds and/or derivatives thereof, natural and/or synthetic, including racemic mixtures, enantiomers, diastereomers, hydrates, salts, solvates and metabolites, etc.

A suitable carrier may include any carrier in the art known for plant essential oils so long as the carrier does not adversely effect the compositions of the present invention. The term "carrier" as used herein means an inert or fluid material, which may be inorganic or organic and of synthetic or natural origin, with which the active compound is mixed or formulated to facilitate its application to the container or carton or other object to be treated, or its storage, transport and/or handling. In general, any of the materials customarily employed in formulating repellents, pesticides, herbicides, or fungicides, are suitable. The compositions of the present invention may be employed alone or in the form of mixtures with such solid and/or liquid dispersible carrier vehicles and/or other known compatible active agents such as other repellants, pesticides, or acaricides, nematicides, fungicides, bactericides, rodenticides, herbicides, fertilizers, growth-regulating agents, etc., if desired, or in the form of particular dosage preparations for specific application made there from, such as solutions, emulsions, suspensions, powders, pastes, and granules which are thus ready for use. The compositions of the present invention can be formulated or mixed with, if desired, conventional inert pesticide diluents or extenders of the type usable in conventional insect control agents, e.g. conventional dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc.

The compositions of the present invention may further comprise surface-active agents. Examples of surface-active agents, i.e., conventional carrier vehicle assistants, that may be employed with the present invention, comprise emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers, magnesium stearate, sodium oleate, etc.); and/or dispersing agents such as lignin, sulfite waste liquors, methyl cellulose, etc.

The compositions of the present invention may be used to control insects by either treating a host directly, or treating an area in which the host will be located. For example, the host may be treated directly by using a cream or spray formulation, which may be applied externally or topically, e.g., to the skin of a human. A composition could be applied to the host, for example, in the case of a human, using formulations of a variety of personal products or cosmetics for use on the skin or hair. For example, any of the following could be used: fragrances, colorants, pigments, dyes, colognes, skin creams, skin lotions, deodorants, talcs, bath oils, soaps, shampoos, hair conditioners and styling agents.

In the case of an animal, human or non-human, the host may also be treated directly by using a formulation of a composition that is delivered orally. For example, a composition could be enclosed within a liquid capsule and ingested.

An area may be treated with a composition of the present invention, for example, by using a spray formulation, such as an aerosol or a pump spray, or a burning formulation, such as a candle or a piece of incense containing the composition. Of course, various treatment methods may be used without departing from the spirit and scope of the present invention.

For example, compositions may be comprised in household products such as: air fresheners (including "heated" air fresheners in which insect repellent substances are released upon heating, e.g. electrically, or by burning); hard surface cleaners; or laundry products (e.g. laundry detergent-containing compositions, conditioners).

The present invention is further illustrated by the following specific but non-limiting examples. The following examples are prophetic, notwithstanding the numerical values, results and/or data referred to and contained in the examples. Examples 1 through 5 relate to the preparation of a cell line expressing the tyramine receptor (TyrR) and screening of compositions using this cell line. Examples 6 through 11 relate to the preparation of a cell line expressing the Or83b receptor, preparation of a cell line expressing the Or43a receptor, and screening of compositions using these cell lines. Examples 12 through 34 relate to the determination of the repellant effect and/or a pesticidal effect of compositions.

EXAMPLE 1

Preparation of Stably Transfected Schmeider Cell Lines with Tyramine Receptor (TyrR)

A. PCR Amplification and Subcloning Drosophika Melanogaster Tyramine Receptor

Tyramine receptor is amplified from *Drosophila melanogaster* head cDNA phage library GH that is obtained through the Berkeley Drosophila Genome Project (Baumann, A., 1999, Drosophila melanogaster mRNA for octopamine receptor, splice variant 1B NCBI direct submission, Accession AJ007617). The nucleic acid sequence and the peptide sequence of TyrR are set forth in SEQ ID NO: 1 and SEQ ID NO: 2, respectively. Phage DNA is purified from this library using a liquid culture lysate. (Baxter, et al., 1999, Insect Biochem Mol Biol 29, 461-467). Briefly, oligonucleotides that are used to amplify the open reading frame of the Drosophila tyramine receptor (TyrR) (Han, et al., 1998, J Neurosci 18, 3650-3658; von Niekisch-Rosenegk, et al., 1996. Insect Biochem Mol Biol 26, 817-827) consist of the 5' oligonucleotide: 5'gccgaattcgccaccATGCCATCGGCA-GATCAGATCCTG 3' (SEQ ID NO: 7) and 3' oligonucleotide: 5'taatctagaTCAATTCAGGCCCAGAAGTCGCTTG 3' (SEQ ID NO: 8). Capitalized letters match the tyramine receptor sequence. An added Kozak sequence (Grosmaitre, X., Jacquin-Joly, E., 2001 Mamestra brassicae putative octopamine receptor (OAR) mRNA, complete cds. NCBI direct submission, Accession AF43878) is indicated by underlined nucleotides. The 5' oligonucleotide also contains an EcoR I site and the 3' oligonucleotide a Xba I site. The PCR is performed using Vent polymerase (New England Biolabs) with the following conditions: about 95° C., about 5 min for about 1 cycle; about 95° C., about 30 sec; and about 70° C., about 90 sec for about 40 cycles; and about 70° C., about 10 min for about 1 cycle.

The PCR product is digested with EcoR I and Xba I, subcloned into pCDNA 3 (Invitrogen) and sequenced on both strands by automated DNA sequencing (Vanderbilt Cancer Center). When this open reading frame is translated to protein, it is found to correctly match the published tyramine receptor sequence (Saudou, et al., The EMBO Journal vol 9 no 1, 6-617). For expression in Drosophila Schneider cells, the TyrR ORF is excised from pCDNA3 and inserted into pAC5.1/V5-His(B) [pAc5(B)] using the Eco RI and Xba I restriction sites.

For transfection, *Drosophila Schneider* cells are stably transfected with pAc5(B)-TyrR ORF using the calcium phosphate-DNA coprecipitation protocol as described by Invitrogen Drosophila Expression System (DES) manual. The precipitation protocol is the same for either transient or stable transfection except for the use of an antibiotic resistant plasmid for stable transfection. At least about ten clones of stably transfected cells are selected and separately propagated. Stable clones expressing the receptors are selected by whole cell binding/uptake using $^3$H-tyramine. For this assay, cells are washed and collected in insect saline (170 mM NaCl, 6 mM KCl, 2 mM NaHCO$_3$, 17 mM glucose, 6 mM NaH$_2$PO$_4$, 2 mM CaCl$_2$, and 4 mM MgCl$_2$). About 3 million cells in about 1 mL insect saline are incubated with about 4 nM $^3$H-tyramine at about 23° C. for about 5 minutes. Cells are centrifuged for about 30 seconds and the binding solution is aspirated. The cell pellets are washed with about 500 µL insect saline and the cells are resuspended and transferred to scintillation fluid. Nonspecific binding is determined by including about 50 µM unlabeled-tyramine in the reaction. Binding is quantified counting radioactivity using a using a Liquid Scintillation β-counter (Beckman, Model LS1801).

B. Selection of Clones Having the Highest Level of Functionally Active Tyramine Receptor Protein Tyramine receptor binding/uptake is performed to determine which of the transfected clones have the highest levels of functionally active tyramine receptor protein. There are about 10 clonal lines for tyramine receptor and about 2 pAc (B) for control. $^3$H-tyramine (about 4 nM/reaction) is used as a tracer, with and without about 50 µM unlabeled tyramine as a specific competitor. For this assay, cells are grown in plates and are collected in about 3 ml of medium for cell counting and the number of cells is adjusted to about $3 \times 10^6$ cells/ml. About two pAcB clones are used in parallel as controls. About 1 ml cell suspension is used per reaction. Based on specific binding, about 3 clones express a high level of active tyramine receptor protein. The clone having the highest specific tyramine receptor binding (about 90%), is selected for further studies. The selected clone is propagated and stored in liquid nitrogen. Aliquot of the selected clone are grown for whole cell binding and for plasma membrane preparation for kinetic and screening studies. The control pAcB does not demonstrate any specific binding for the tyramine receptor.

C. Efficacy of Schneider Cells Transfected with Tyramine Receptor for Screening Compositions for Tyramine Receptor Interaction Cells transfected with the tyramine receptor (about $1 \times 10^6$ cells/ml) are cultured in each well of a multi-well plate. About 24 hours after plating the cells, the medium is withdrawn and replaced with about 1 ml insect saline (about 23° C.). Different concentrations of $^3$H-tyramine (about 0.1-10 nM) are added with and without about 10 µM unlabeled tyramine and incubated at room temperature (RT). After about a 20 minute incubation, the reaction is stopped by rapid aspiration of the saline and at least one wash with about 2 ml insect saline (about 23° C.). Cells are solubilized in about 300 µl 0.3M NaOH for about 20 min at RT. Solubilized cells are transferred into about 4 ml Liquid Scintillation Solution (LSS) and vigorously vortexed for about 30 sec before counting the radioactivity using a Liquid Scintillation β-counter (Beckman, Model LS1801) (LSC).

With reference to FIG. 1, receptor specific binding data is expressed as fmol specific binding per $1 \times 10^6$ cells and measured as a function of $^3$H-tyramine concentration. Specific binding values are calculated as the difference between values in the absence of and values in the presence of about 10 µM unlabeled tyramine. As shown in FIG. 1, the maximum specific binding occurs at about 5 nM $^3$H-tyramine. Untransfected cells do not respond to tyramine at concentration as high as about 100 µM.

To study the kinetics of the tyramine receptor in stably transfected cells with pAcB-TyrR, crude membrane fractions are prepared from the transfected cells and used to calculate the equilibrium dissociation constant ($K_d$), Maximum Binding Capacity ($B_{max}$), equilibrium inhibitor dissociation constant ($K_i$) and $EC_{50}$ (effective concentration at which binding is inhibited by 50%). A preliminary study to determine the optimum concentration of membrane protein for receptor binding activity is performed. In this study, different concentrations of protein (about 10-50 µg/reaction) are incubated in about 1 ml binding buffer (50 mM Tris, pH 7.4, 5 mM $MgCl_2$ and 2 mM ascorbic acid). The reaction is initiated by the addition of about 5 nM $^3$H-tyramine with and without about 10 µM unlabeled tyramine. After about 1 hr incubation at room temperature, reactions are terminated by filtration through GF/C filters (VWR), which have been previously soaked in about 0.3% polyethyleneimine (PEI). The filters are washed one time with about 4 ml ice cold Tris buffer and air dried before the retained radioactivity is measured using LSC. Binding data is analyzed by curve fitting (GraphPad software, Prism). The data demonstrates no differences between about 10, 20, 30 and 50 µg protein/reaction in tyramine receptor specific binding. Therefore, about 10 µg protein/reaction is used.

To determine $B_{max}$ and $K_d$ values for tyramine receptor (TyrR) in membranes expressing TyrR, saturation binding experiments are performed. Briefly, about 10 µg protein is incubated with $^3$H-tyramine at a range of concentrations (about 0.2-20 nM). Binding data is analyzed by curve fitting (GraphPad software, Prism) and the $K_d$ for tyramine binding to its receptor is determined.

To determine the affinities of several ligands for TyrR, increasing concentration of several compounds are tested for their ability to inhibit binding of about 2 nM $^3$H-tyramine. For both saturation and inhibition assays total and non-specific binding is determined in the absence and presence of about 10 µM unlabeled-tyramine, respectively. Receptor binding reactions are incubated for about 1 hr at room temperature (RT) in restricted light. Reactions are terminated by filtration through GF/C filters (VWR), which have been previously soaked in about 0.3% polyethyleneimine (PEI). The filters are washed one time with about 4 ml ice cold Tris buffer and air dried before retained radioactivity is measured using LSC. Binding data is analyzed by curve fitting (GraphPad software, Prism).

Figure 2:
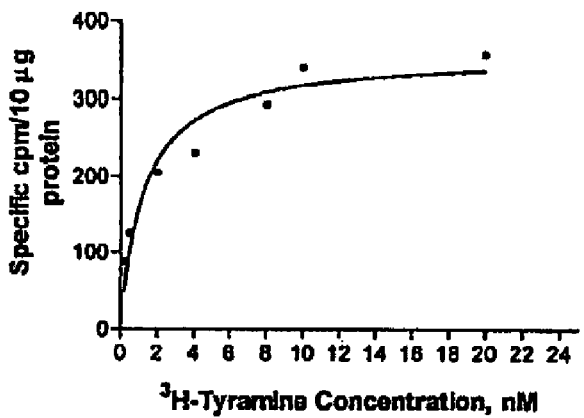
FIG. 2 shows the saturation binding curve of $^3$H-tyramine in membranes prepared from Schneider cells expressing the tyramine receptor after incubation with $^3$H-tyramine at various concentrations in the presence or absence of unlabeled tyramine.

With reference to FIG. 2, depicting a saturation binding curve of $^3$H-tyramine ($^3$H-TA) to membranes prepared from Schneider cells expressing tyramine receptor, $^3$H-tyramine has a high affinity to tyramine receptor in the stably transfected cells with pAcB-TyrR with $K_d$ determined to be about 1.257 nM and $B_{max}$ determined to be about 0.679 pmol/mg protein.

Figure 3:
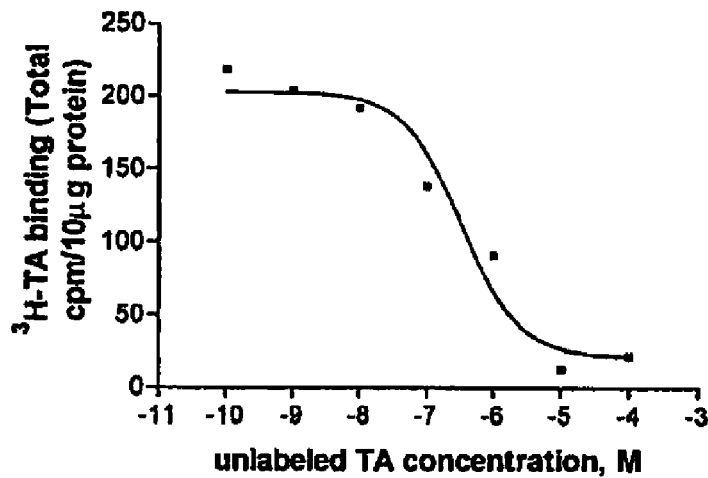
FIG. 3 shows the inhibition binding curve of $^3$H-tyramine to membranes prepared from Schneider cells expressing the tyramine receptor after incubation with $^3$H-tyramine in the presence and absence of different concentrations of the unlabeled tyramine.

With reference to FIG. 3, depicting the inhibition binding of $^3$H-tyramine ($^3$H-TA) to membranes prepared from Schneider cells expressing tyramine receptor in the presence and absence of various concentrations of unlabeled tyramine (TA), the $EC_{50}$ and the $K_i$ for tyramine against its receptor in Schneider cells expressing tyramine receptor are about 0.331 µM and 0.127 µM, respectively.

Figure 4:
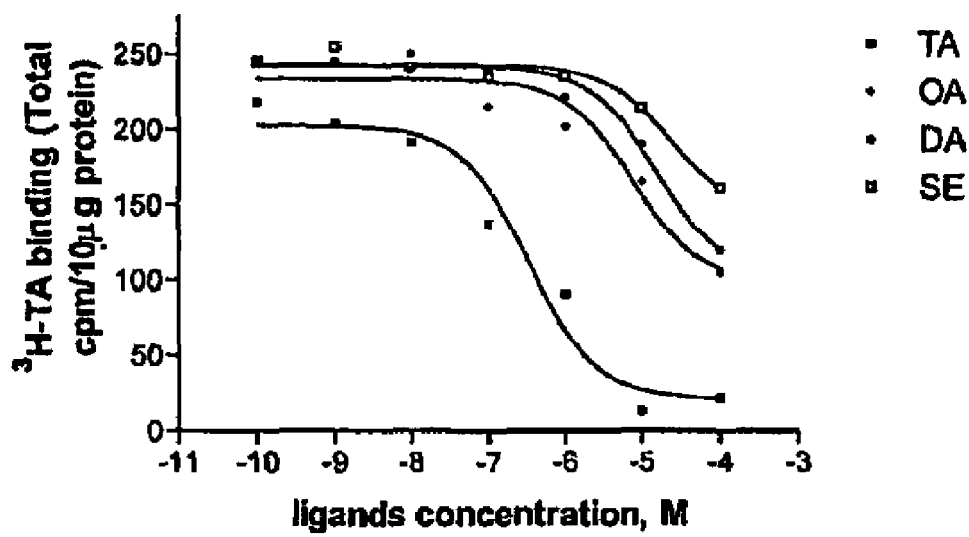
FIG. 4 shows the inhibition binding curve of $^3$H-tyramine to membranes prepared from Schneider cells expressing the tyramine receptor in the presence and absence of different concentrations of the unlabeled ligands: tyramine (TA), octopamine (OA), dopamine (DA), and serotonin (SE)

In order to determine the pharmacological profile of tyramine receptor (TyrR), the ability of a number of putative Drosophila neurotransmitters to displace $^3$H-tyramine ($^3$H-TA) binding from membranes expressing tyramine receptor is tested. With reference to FIG. 4, depicting inhibition binding of $^3$H-Tyramine to membranes prepared from Schneider cells expressing tyramine receptor in the presence and absence of different concentrations of unlabeled ligands (including Tyramine (TA), Octopamine (OA), Dopamine (DA), and Serotonin (SE)), tyramine displays the highest affinity ($K_i$ of about 0.127 µM, $EC_{50}$ of about 0.305 µM) for the Drosophila TyrR. Octopamine, dopamine and serotonin were less efficient than tyramine at displacing $^3$H-tyramine binding.

With reference to Table A, setting forth the $K_i$ and $EC_{50}$ of the ligands, the rank order of potency is as follows: tyramine>octopamine>dopamine>serotonin, showing the likelihood that the stably transfected Schneider cells are expressing a functionally active tyramine receptor.

TABLE A

| Ligand | $K_i$ (µM) | $EC_{50}$ (µM) |
| --- | --- | --- |
| Tyramine (TA) | 0.127 | 0.305 |
| Octopamine (OA) | 2.868 | 7.456 |
| Dopamine (DA) | 5.747 | 14.940 |
| Serotonin (SE) | 8.945 | 23.260 |

As such, Schneider cells expressing tyramine receptor are effective as a model for studies and screening for compositions that interact with the tyramine receptor.

EXAMPLE 2

Treatment of Cells Expressing the Tyramine Receptor and Effect of Compositions of Intracellulat [cAMP]

Cells are grown on dishes and the media changed the day before the treatment. When cells are approximately 95% confluent, media is aspirated and the cells are washed one time with about 5 mL of about 27° C. insect saline (170 mM NaCl, 6.0 mM KCl, 2.0 mM NaHCO3, 17.0 mM glucose, 6.0 mM NaH2PO4, 2.0 mM CaCl2, 4.0 mM MgCl2; pH 7.0). About 20 mL of insect saline is added, and cells are harvested by gentle scraping. An aliquot of the cells is counted by hemocytometer, and the cells are then centrifuged for about 5 minutes at about 1000 RPM. Cells are resuspended to give about $3\times10^6$ cells per mL. IBMX is added to about 200 µM. Then about 1 mL of cell suspension is aliquoted for treatment. Forskolin (cAMP inducing agent), tyramine or different composition candidates are added, and the cells are incubated at about 27° C. for about 10 minutes.

Treated cells are centrifuged at about 13000 g for about 10 seconds. The solution is aspirated and about 1 mL of about −20° C. 70% ethanol is added. The cell pellet is disrupted by vortexing and the samples placed at about −20° C. overnight. Following the ethanol extraction, cellular debris is pelleted by centrifugation at about 13000 g for about 5 minutes. The supernatant is transferred to a tube and lyophilized to dryness in a rotary speed-vac. The resulting extract is resuspended in about 100 µL TE and used for the cAMP assay.

The cAMP assay is based on competition binding between endogenous cAMP and $^3$H-cAMP to a cAMP binding protein. The $^3$H-cAMP Biotrak system (Amersham Biosciences) is used for this assay as per the manufacturer's instructions. Briefly, about 50 µL of the cellular extract is incubated with about 50 µL $^3$H-cAMP and about 100 µL cAMP binding protein in an ice bath for about 2-4 hours. Charcoal (about 100 µL) is then added and the solution centrifuged for about 3 minutes at about 4° C. About 200 µL of the reaction mixture is removed and levels of $^3$H-cAMP are determined by scintillation counting. Levels of endogenous cAMP from the cells are calculated using a standard curve with cold cAMP ranging from about 0 to 16 pmol per reaction.

EXAMPLE 3

Treatment of Cells Expressing the Tyramine Receptor and Effect of Compositions of Intracellulat [$Ca^{2+}$]

Intracellular calcium ion concentrations ([$Ca^{2+}$]i) are measured by using the acetoxymethyl (AM) ester of the fluorescent indicator fura-2 (Enan, et al., Biochem. Pharmacol vol 51, 447-454). In this study, cells expressing tyramine receptor are grown under standard conditions. A cell suspension is prepared in assay buffer (140 mM NaCL, 10 mM HEPES, 10 mM glucose, 5 mM KCl, 1 mM CaCl2, 1 mM MgCl2) and cell number adjusted to about $2 \times 10^6$ cells per ml. Briefly, about 1.0 ml cell suspension (about $2 \times 10^6$ cells) is incubated with about 5 µM Fura 2/AM for about 30 min at about 28° C. After incubation, the cells are pelleted at about 3700 rpm for about 10 sec at room temperature and then resuspended in about 1.5 ml assay buffer. [$Ca^{2+}$]i changes are analyzed in spectrofluorometer in the presence and absence of test chemicals. Excitation wave lengths are about 340 nm (generated by $Ca^{2+}$-bound fura-2) and about 380 nm (corresponding to $Ca^{2+}$-free fura-2). The fluorescence intensity is monitored at an emission wave length of about 510 nm. No absorbance of fluorescence artifacts are observed with any of the compounds used. The ratio of about 340/380 nm is calculated and plotted as a function of time.

EXAMPLE 4

Effect of Lilac Flower Oil and Black Seed Oil on Tyramine Receptor Binding Activity in Cells Expressing the Tyramine Receptor To determine whether specific oils, namely, Lilac Flower Oil (LFO) and Black seed Oil (BSO), interact and regulate the functional expression of tyramine receptor, membranes from stably transfected and untransfected Schneider cells are analyzed for $^3$H-Tyramine binding.

Figure 5:
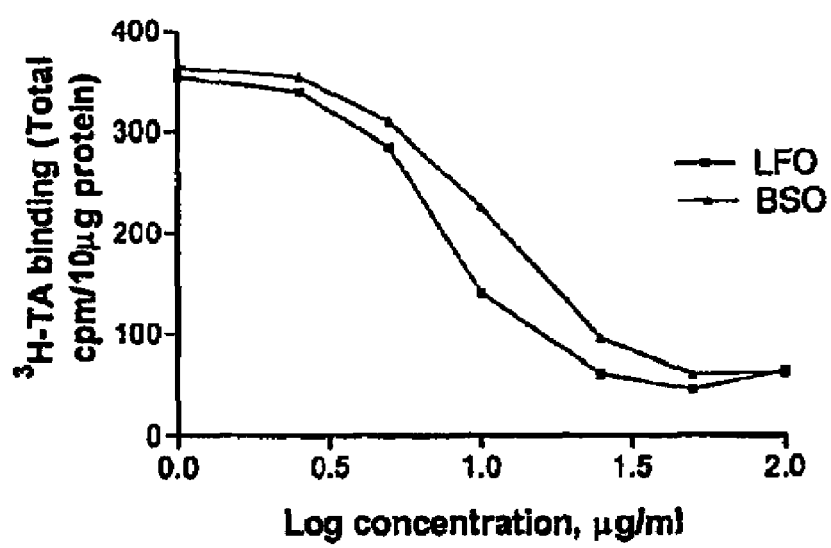
FIG. 5 shows the Inhibition binding curve of $^3$H-tyramine to membranes prepared from Schneider cells expressing the tyramine receptor after incubation with $^3$H-tyramine in the presence and absence of different concentrations of Lilac Flower Oil (LFO) and Black Seed Oil (BSO)

For the interaction with $^3$H-Tyramine at the receptor sites, the same binding protocol as described above is used. A dose-response of LFO and BSO (about 1-100 µg/ml) is performed to determine their effect on the inhibition binding of $^3$H-Tyramine to membranes prepared from Schneider cells expressing the tyramine receptor. With reference to FIG. 5, depicting the inhibition binding of $^3$H-Tyramine to membranes prepared from Schneider cells expressing tyramine receptor in the presence and absence of different concentrations of LFO and BSO, the inhibition of $^3$H-Tyramine to its receptor is demonstrated in response to treatment with LFO and BSO in a dose-dependent manner. The $EC_{50}$ values for LFO and BSO are approximately in the neighborhood of 10 µg/ml and 20 µg/ml, respectively.

Figure 6:
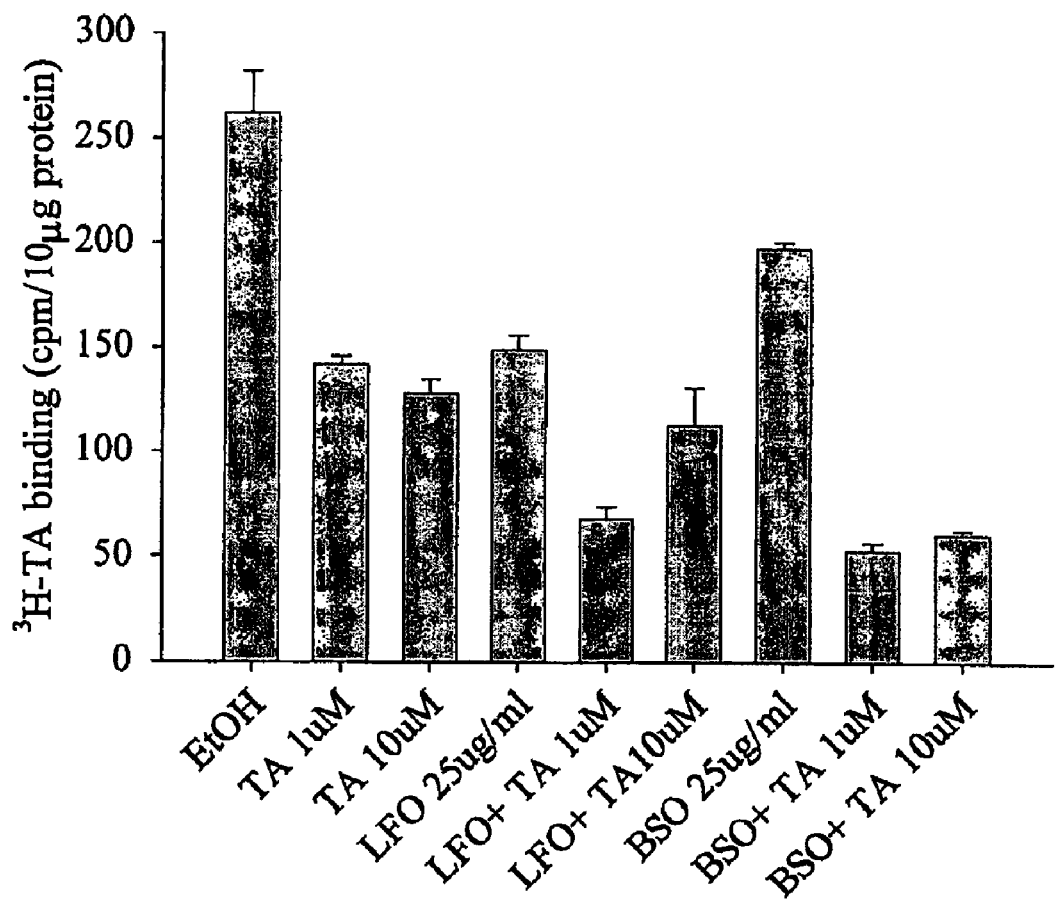
FIG. 6 shows the inhibition binding of $^3$H-tyramine (3H-TA) to membranes prepared from Schneider cells expressing the tyramine receptor after incubation with $^3$H-tyramine in the presence and absence of either LFO or BSO or in combination with different concentrations of unlabeled tyramine (TA)

Turning now to FIG. 6, depicting the inhibition binding of $^3$H-tyramine to membranes prepared from Schneider cells expressing tyramine receptor in the presence and absence of either LFO or BSO or in combination with about 1 and 10 µM unlabeled Tyramine, LFO (about 25 µg/ml) by itself inhibits the binding of $^3$H-Tyramine to its receptor. This effect is equivocal to the effect of about 10 µM (about 1.74 µg/ml) unlabeled tyramine. In addition, LFO potentiates the potency of unlabeled Tyramine against $^3$H-Tyramine binding only when unlabeled tyramine is used at about 1 µM. On the other hand, BSO (about 25 µg/ml) is less efficacious against $^3$H-Tyramine binding than LFO. BSO, however, significantly increases the potency of unlabeled-Tyramine against $^3$H-Tyramine binding regardless the concentration of unlabeled Tyramine. The two oils do not show any effect on $^3$H-Tyramine binding in untransfected Schneider cells.

As such, it appears that LFO and BSO interact with the tyramine receptor differently. Not wishing to be bound by theory or mechanism, it is likely that LFO and tyramine compete at the same binding sites, while BSO acts at different sites of the receptor than the endogenous ligand (tyramine). Certain other oils, including those expressly set forth in this application, also interact with the tyramine receptor.

EXAMPLE 5

Effect of Lilac Flower Oil and Black Seed Oil on Intracellular [cAMP] in Cells Expressing the Tyramine Receptor To examine test chemical-dependent coupling of the tyramine receptor, pAcB-TyrR is stably expressed in Schneider cells. Transfected and untransfected cells are treated with tyramine (about 10 µM), LFO (about 25 µg/ml) and BSO (about 25 µg/ml) in the presence and absence of forskolin (FK) (about 10 µM). cAMP production is measured using the $^3$H-cAMP assay kit (Amersham) as described above.

Figure 7:
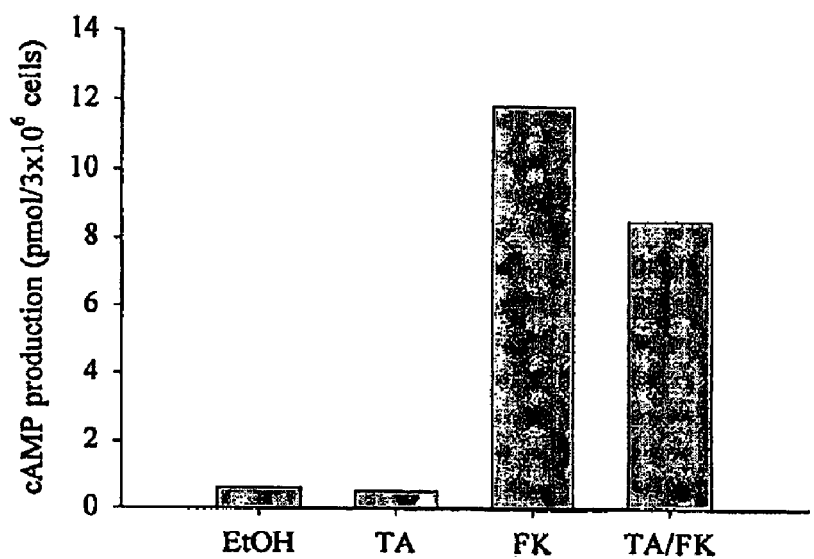
FIG. 7 shows tyramine dependent changes in cAMP levels in Schneider cells expressing the tyramine receptor in the presence and absence of forskolin and tyramine.
Figure 8:
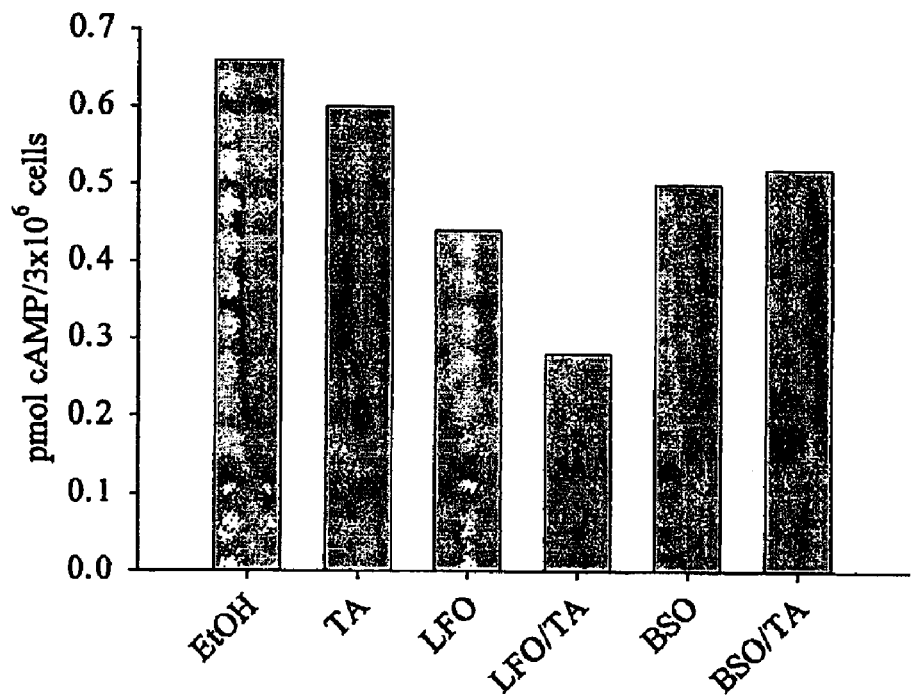
FIG. 8 shows tyramine dependent changes in cAMP levels in Schneider cells expressing the tyramine receptor treated with Lilac Flower Oil and Black Seed Oil in the presence and absence of forskolin and tyramine.
Figure 9:
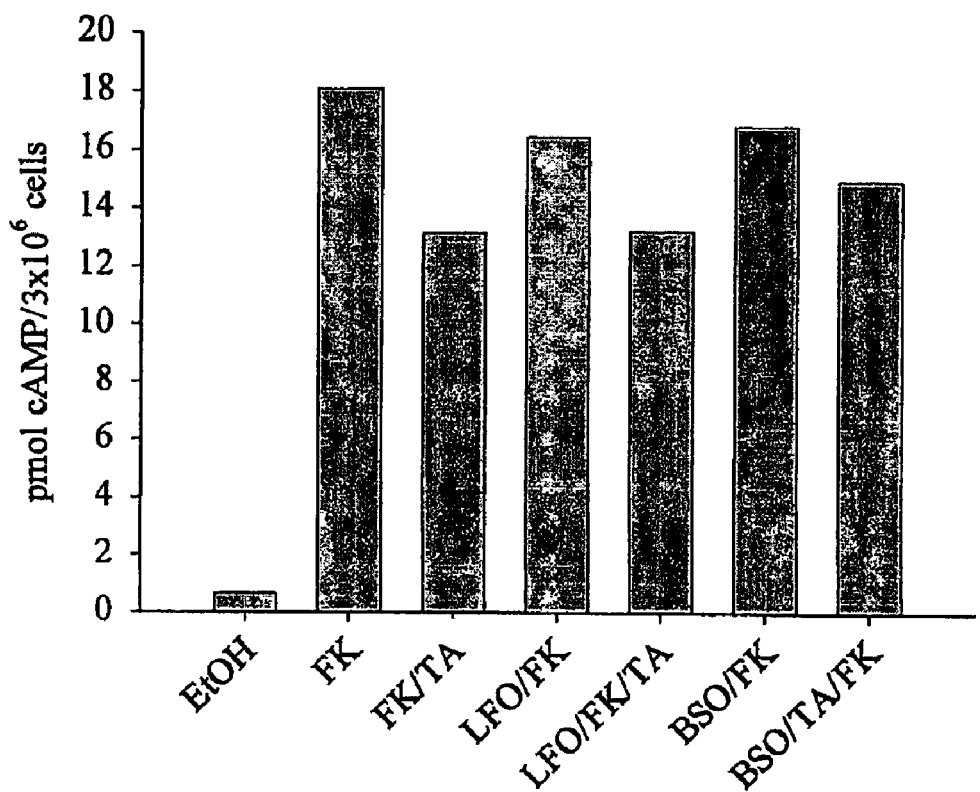
FIG. 9 shows tyramine dependent changes in cAMP levels in Schneider cells expressing the tyramine receptor after treatment with forskolin in the presence and absence of tyramine, Lilac Flower Oil and Black Seed Oil.

To ensure that the cAMP cascade in this cell model is functionally active, forskolin, a cAMP inducer, is used as standard agent. As shown in FIGS. 7 through 9, which depict tyramine-dependent changes in cAMP levels in Schneider cells expressing tyramine receptor following treatment with LFO (about 25 µg/ml) and BSO (about 25 µg/ml) in the presence and absence of tyramine (about 10 µM) and forskolin (about 10 µM), there is about a 19-fold increase in the cAMP levels only in transfected cells in response to treatment with forskolin as compared to the basal level of cAMP in cells treated only with the solvent (ethanol).

Tyramine, on the other hand, induces a slight decrease (about 10%) in cAMP production. Tyramine, however, significantly antagonizes forskolin-stimulated cAMP levels in cells expressing tyramine receptor, suggesting that tyramine receptor couples to $G_{\alpha i/o}$ in the presence of tyramine, as shown in FIG. 7. About a 34% and 25% decrease in cAMP level are found only in transfected cells in response to treatment with LFO and BSO respectively (FIG. 8). While tyramine potentiates the effect of LFO on cAMP production in the tyramine-receptor transfected cells, co-treatment of BSO and tyramine does not induce any changes in cAMP level beyond the effect of BSO by itself, as shown in FIG. 8. The LFO- and BSO-decreased cAMP levels in Schneider cells expressing tyramine receptor is diminished in the presence of forskolin, as shown in FIG. 9.

Treatment with certain other plant essential oils, including those expressly set forth in the application, also result in changes in intracellular cAMP levels in cells expressing tyramine receptor.

EXAMPLE 6

Preparation of Stably Transfected Schneider Cell Lines with Olfactory Receptors (Or83b and Or43a)

A. RT-PCR Amplification and Subcloning *Drosophila Melanogaster* Olfactouy Receptors Or83b and Or43a Total RNA is prepared from the head and antenna of wild type Drosophila melanogaster using Trizol Reagent (Invitrogen). They are homogenized in the Trizol using a motor driven teflon pestle and glass homogenizer. RNA is then prepared as per the manufacturer's instructions and includes removal of proteoglycans and polysaccharides by precipitation. The total RNA is reverse transcribed using oligo-dT as a primer and MuLV reverse transcriptase (Applied Biosystems). To PCR amplify the open reading frames, the following oligonucleotides are used: Or83b Sense 5'taagcggccg-cATGACAACCTCGATGCAGCCGAG 3' (SEQ ID NO: 9); Or83b Antisense 5'ataccgcggCTTGAGCTGCACCAGCAC-CATAAAG 3' (SEQ ID NO: 10); Or43a Sense 5'taagcggccg-cATGACAATCGAGGATATCGGCCTGG 3' (SEQ ID NO: 11); and Or43a Antisense 5'ataccgcggTTTGCCGGT-GACGCCACGCAGCATGG 3' (SEQ ID NO: 12). Capitalized letters match the Or83b and Or43a receptors sequence. The Sense oligonucleotides contain Not I sites and the antisense oligonucleotides contain Sac II sites. Both restriction sites are indicated by underlined nucleotide. The antisense oligonucleotides do not contain stop codons so the V5 epitope from the pAC 5.1 plasmid will be in frame with the translated proteins. For PCR amplification of Or83b, Vent polymerase (New England Biolabs) is used with the following conditions: about 95° C., about 5 min for about 1 cycle; about 95° C., about 30 sec; and about 70° C., about 90 sec for about 40 cycles; and about 70° C., about 10 min for about 1 cycle. For PCR amplification of Or43a, the Failsafe PCR premix selection kit (Epicentre Technologies) is used with the following conditions: about 95° C., about 5 min for about 1 cycle; about 95° C., about 30 sec; about 60° C., about 30 sec and about 70° C., about 90 sec for about 50 cycles; and about 70° C., about 10 min for about 1 cycle. The Failsafe premix buffer F yields the correctly sized product. The PCR products are digested with Sac II and Not I, gel purified and ligated into pAC 5.1/V5 His B (Invitrogen). Inserts are sequenced on both strands by automated flourescent sequencing (Vanderbilt Cancer Center). Both the Or83b open reading frame and Or43a open reading frame code for identical proteins as compared to sequence information on PubMed and found in the genomic sequence on the Web site. The nucleic acid sequence and the peptide sequence of Or43a are set forth in SEQ ID NO: 3 and SEQ ID NO: 4, respectively. The nucleic acid sequence and the peptide sequence of Or83b are set forth in SEQ ID NO: 5 and SEQ ID NO: 6, respectively.

For transfection, *Drosophila Schneider* cells are stably transfected with pAc5(B)-Or83b ORF or pAc5(B)-Or43a ORF using the calcium phosphate-DNA coprecipitation protocol as described by Invitrogen Drosophila Expression System (DES) manual as described above. At least about ten clones of stably transfected cells with either Or83b or Or43a are selected and separately propagated. Stable clones are analyzed to test whether they express corresponding mRNA using RT-PCR method. RNA is prepared from cells using Trizol as per the manufacturer's instructions. Total RNA is reverse transcribed with MuLV Reverse Transcriptase. PCR is performed using Vent polymerase and the following primers: Or83b sense and Or83b antisense; Or43a sense and Or43a antisense. PCR products are analyzed by agarose gel electrophoresis and compared to control Schneider cell RNA used. for RT-PCR. A clone that highly expresses Or83b-mRNA or Or43a-mRNA is used in further studies to address protein expression (Western blot), and signaling (cAMP production and [Ca2+]) in response to treatment with tyramine and certain plant essential oils.

RT-PCR is used to determine which clones expressed the Or83b and Or43a genes. Agarose gel analysis indicates that for Or83b, about 4 clones out of about 10 clones yield the correct size product of about 1.46 kb. Likewise, for Or43a, about 2 clones yield the correct size product of about 1.1 kb. Neither of these products is obtained when PCR is performed on the control Schneider cells. Clones expressing the mRNA are chosen for additional studies with the receptor.

Figure 10:
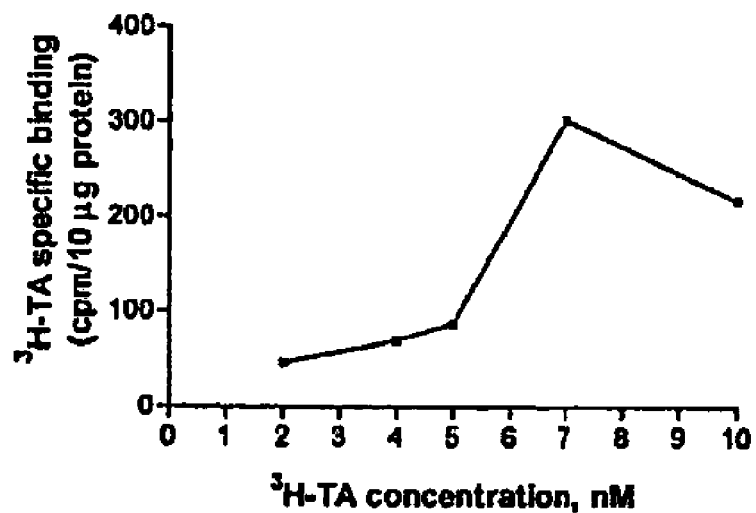
FIG. 10 shows the saturation binding curve of $^3$H-tyramine to membranes prepared from Schneider cells expressing the Or83b receptor.
Figure 11:
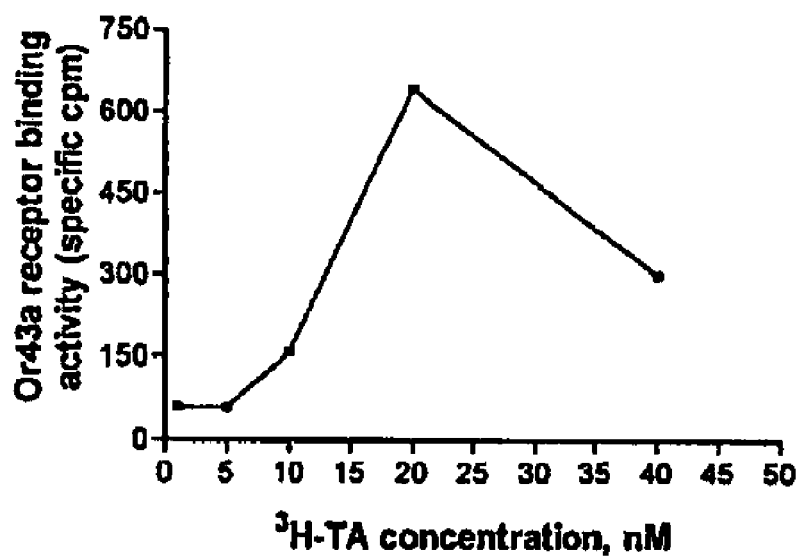
FIG. 11 shows the saturation binding curve of $^3$H-tyramine to membranes prepared from Schneider cells expressing the Or 43a receptor.

B. Efficacy of Schneider Cell Lines Transfected with Or83b Receptor of Or43a Receptor for Screening Compositions for Or83b and Or43a Receptor Interaction To address whether Or83b receptor and Or43a receptor contain a specific binding site for tyramine, membranes expressing Or83b receptor or Or43a receptor are prepared from cells expressing either receptor, as described above, and used for competitive binding with $^3$H-tyramine. The binding assay protocol is exactly as described for cells expressing TyrR, as described above. As shown in FIG. 10, depicting a saturation binding curve of $^3$H-tyramine to membranes prepared from Schneider cells expressing the Or83b receptor in the presence or absence of about 20 µM unlabeled tyramine, and FIG. 11, depicting the same information for the cells expressing the Or43a receptor, $^3$H-Tyramine binds specifically to the Or83b and the Or43a receptors. As set forth in Table B, Tyramine binds to the Or83b receptor with Kd of approximately 96.90 nM and $B_{max}$ of approximately 4.908 pmol/mg protein. For Or43a the corresponding values are Kd of approximately 13.530 nM and Bmax of approximately 1.122 pmol/mg protein.

TABLE B

| Receptor type | $K_i$ (nM) | $B_{max}$ (pmol/mg protein) |
| --- | --- | --- |
| TyrR | 1.257 | 0.679 |
| Or83b | 96.900 | 4.908 |
| Or43a | 13.530 | 1.122 |

EXAMPLE 7

Production of cAMP in Cells Expressing Olfactory Receptors

Figure 12:
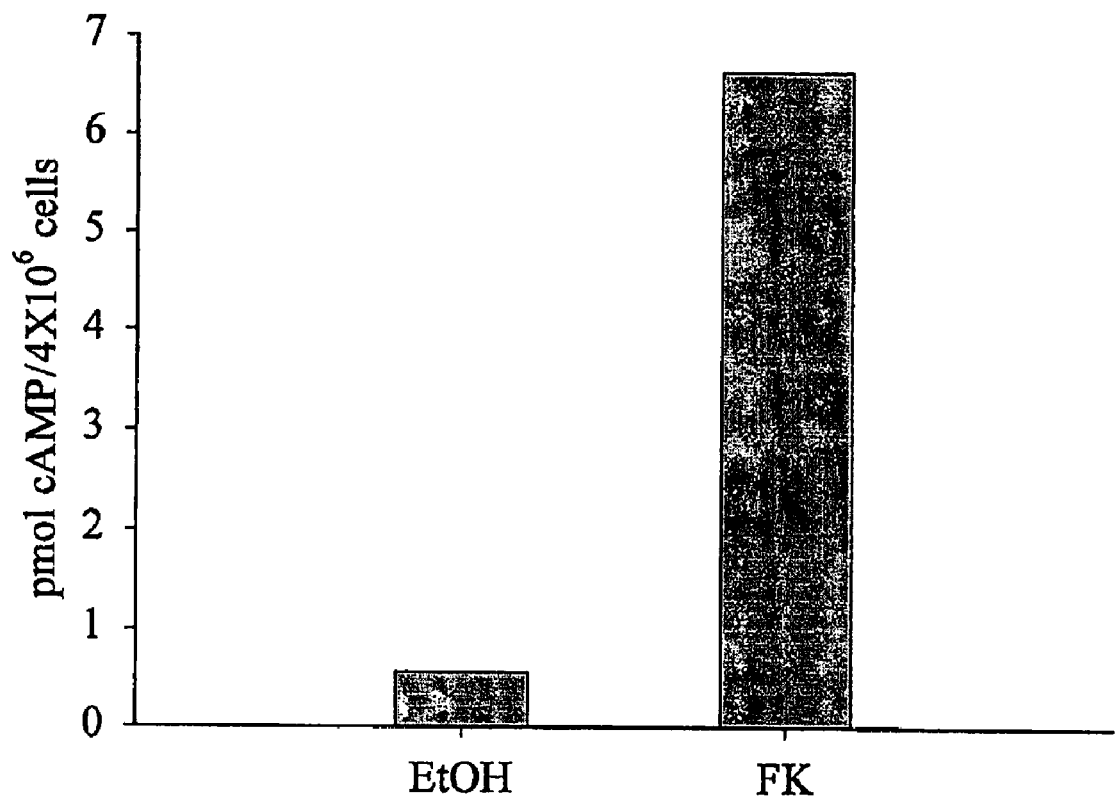
FIG. 12 shows the forskolin-dependent changes in cAMP levels in Schneider cells expressing the Or83b receptor.

To ensure that the cAMP cascade in this cell model is functionally active, forskolin, a cAMP inducer, is used as standard agent. Cyclic-AMP levels are measured using the cAMP assay described above in Example 2. As shown in FIG. 12, depicting forskolin-dependent changes in cAMP levels in the cells expressing Or83b receptor, there is approximately a 13-fold increase from the basel cAMP levels in cells treated with about 10 µM forskolin for about 10 min at room temperature. Similar results are obtained with cells expressing Or43a receptor. As such, the cells expressing olfactory receptors have a functionally active cAMP cascade.

EXAMPLE 8

Intracellular Mobilization of $Ca^{2+}$ in Cells Expressing Olfactory Receptors

Figure 13:
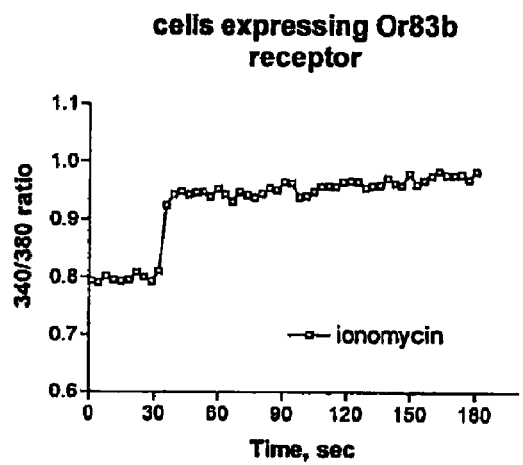
FIG. 13 shows the ionomycin-dependent changes in intracellular $Ca^{2+}$ levels in Schneider cells expressing the Or83b receptor.
Figure 14:
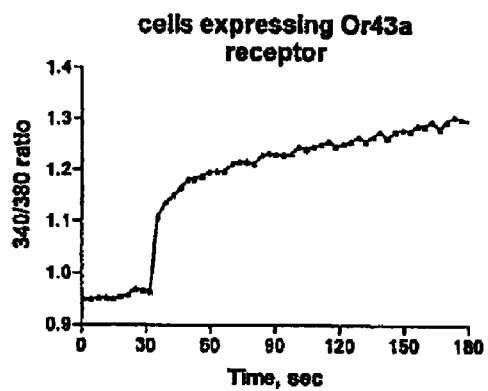
FIG. 14 shows the ionomycin-dependent changes in intracellular $Ca^{2+}$ levels in Schneider cells expressing the Or43a receptor.

Intracellular $Ca^{2+}$ levels are measured using the method described above in Example 3. Calcium mobilization occurs in cells expressing either Or83b or Or43a receptor in response to treatment with ionomycin (a $Ca^{2+}$ inducing agent) and tyramine. Specifically, with reference to FIGS. 13 and 14, in which fluorescence ratio determined from excitation with 340 nm and 380 nm correlates to intracellular calcium levels when about 2 µM ionomycin is added to the Or83b or Or43a expressing cells, a marked increase in intracellular calcium is detected.

Figure 15:
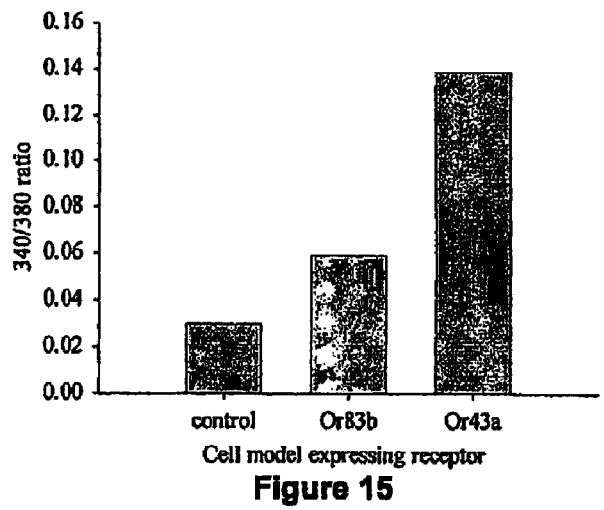
FIG. 15 shows the tyramine-dependent changes in intracellular $Ca^{2+}$ levels in control Schneider cells, Schneider cells expressing the Or83b receptor, and Schneider cells expressing the Or 43a receptor.

Approximately 3.8-fold and 7-fold increases in calcium are found in cells expressing Or83b and Or43a, respectively, in response to treatment with ionomycin. With reference to FIG. 15, testing of the tyramine at about 10 μM can also induce approximately a 1.18-fold increase and 3.5-fold increase in intracellular calcium in cells expressing Or83b and Or43a, respectively.

Collectively, the pharmacological analysis data confirm that these cell models that were transfected with either Or83b receptor gene or Or43a receptor gene are expressing functioning protein receptors.

EXAMPLE 9

Effect of Various Plant Essential Oils on the Binding Activity of Olfactory Receptors and Signaling Pathways Down Stream to the Receptors The cells expressing one of the olfactory receptors are used to investigate the interaction of plant essential oils with these receptors and the signaling cascade downstream of each receptor.

Figure 16:
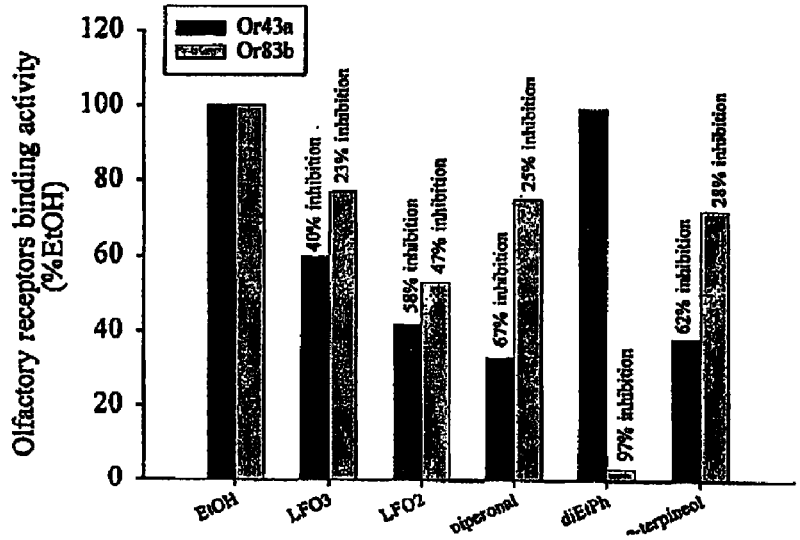
FIG. 16 shows the interaction of various plant essential oils, including, LFO, piperonal, diethyl phthalate, and α-terpineol, with the Or83b and Or43a receptors in Schneider cells expressing the olfactory receptors after incubation with $^3$H-tyramine.

For the binding activity, membranes are prepared from each cell model and used to investigate the interaction of plant essential oil with the receptor binding site. With reference to FIG. 16, the following oils interact with the olfactory receptors: lilac flower oil (LFO), diethyl phthalate, α-terpineol, and piperonal.

Figure 17:
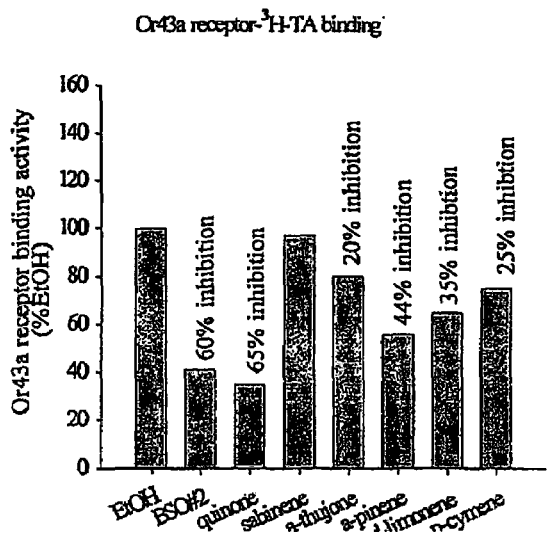
FIG. 17 shows the interaction of various plant essential oils, including, BSO, quinine, sabinene, α-thujone, α-pinene, d-limonene, and p-cymene with the Or43a receptors in Schneider cells expressing the olfactory receptors after incubation with $^3$H-tyramine.
Figure 18:
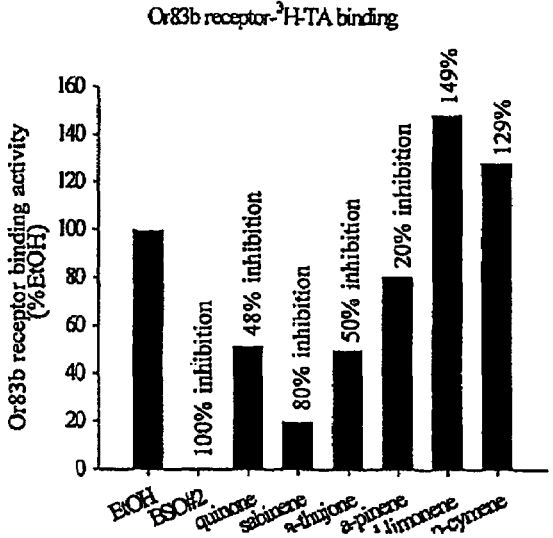
FIG. 18 shows the interaction of various plant essential oils, including, BSO, quinine, sabinene, α-thujone, α-pinene, d-limonene, and p-cymene with the Or83b receptors in Schneider cells expressing the olfactory receptors after incubation with $^3$H-tyramine.

Likewise, with reference to FIGS. 17 and 18, the following oils interact with the olfactory receptors: black seed oil (BSO), α-pinene, quinone,p-cymene, sabinene, α-thujone and d-limonene.

Figure 19:
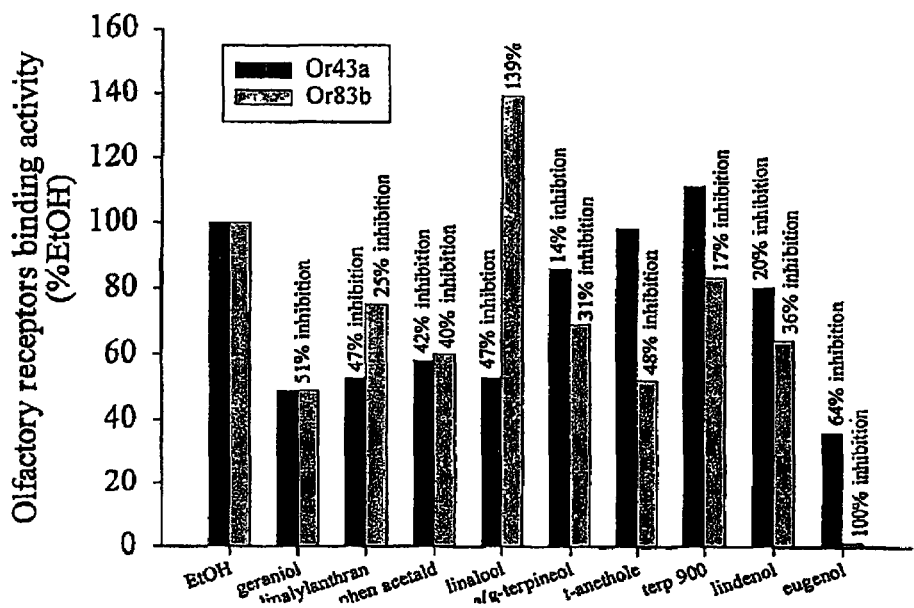
FIG. 19 shows the interaction of various plant essential oils, including, geraniol, linalyl anthranilate, phenyl acetaldehyde, linalool, α-terpineol, t-anethole, terpinene 900, lindenol, and eugenol, with the Or83b and Or43a receptors in Schneider cells expressing the olfactory receptors after incubation with $^3$H-tyramine.
Figure 20:
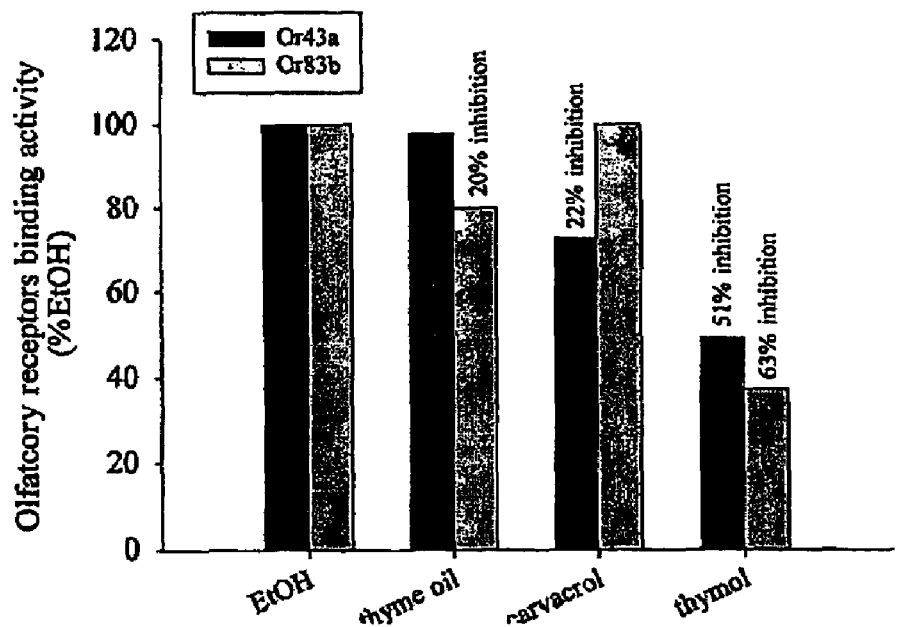
FIG. 20 shows the interaction of various plant essential oils, including, thyme oil, carvacrol, and thymol, with the Or83b and Or43a receptors in Schneider cells expressing the olfactory receptors after incubation with $^3$H-tyramine.
Figure 21:
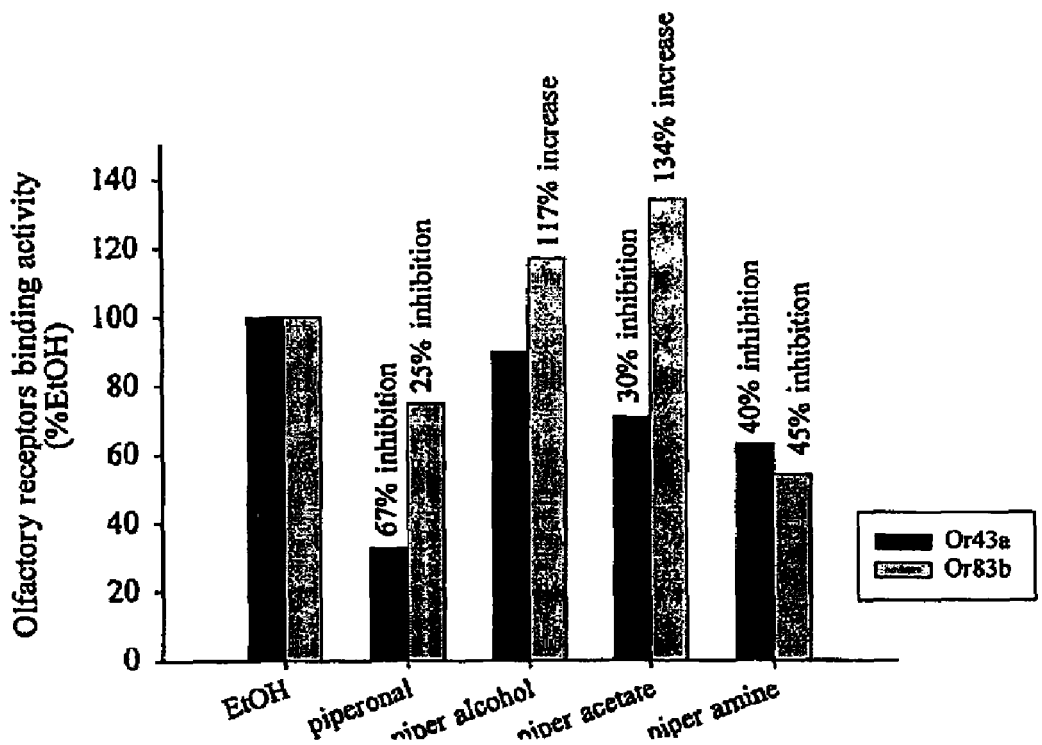
FIG. 21 shows the interaction of various plant essential oils, including, piperonal, piperonyl alcohol, piperonyl acetate, and piperonyl amine, with the Or83b and Or43a receptors in Schneider cells expressing the olfactory receptors after incubation with $^3$H-tyramine.

Similarly, with reference to FIGS. 19 through 21, the following oils also interact with the olfactory receptors: geraniol, linalyl anthranilate, phenyl acetaldehyde, linalool, α-terpineol, t-anethole, terpinene 900, lindenol, eugenol, thyme oil, carvacrol, thymol, piperonal, piperonyl alcohol, piperonyl acetate, and piperonyl amine.

Certain other oils, including those expressly set forth in this application, also interact with the olfactory receptors.

EXAMPLE 10

Figure 22:
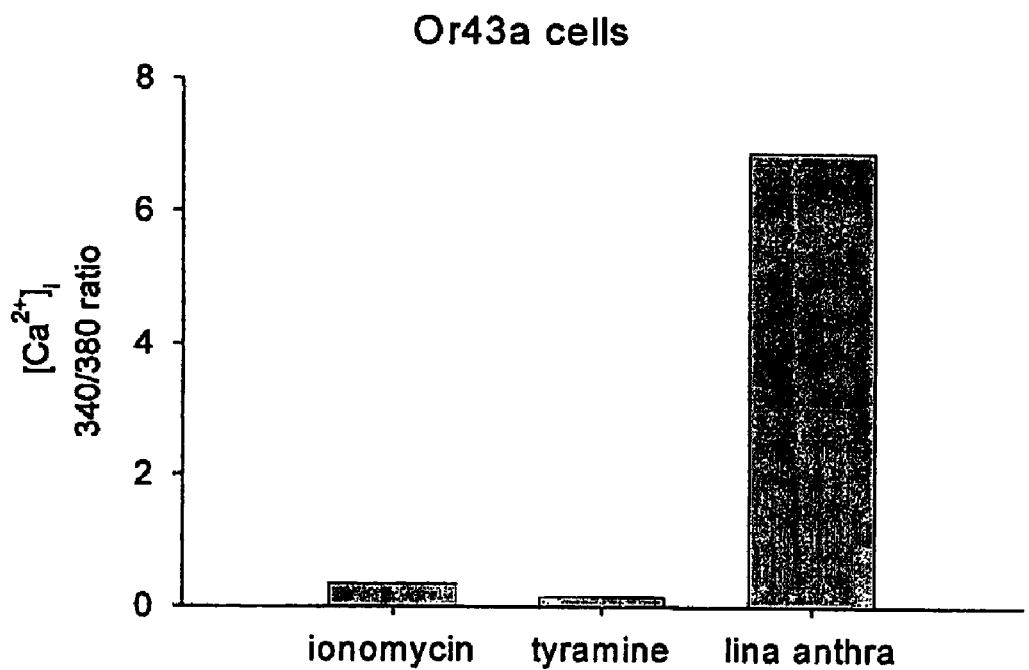
FIG. 22 shows the effect of ionomycin, tyramin, and linalyl anthranilate on intracellular $Ca^{2+}$ levels in Schneider cells expressing the Or43a receptor.
Figure 23:
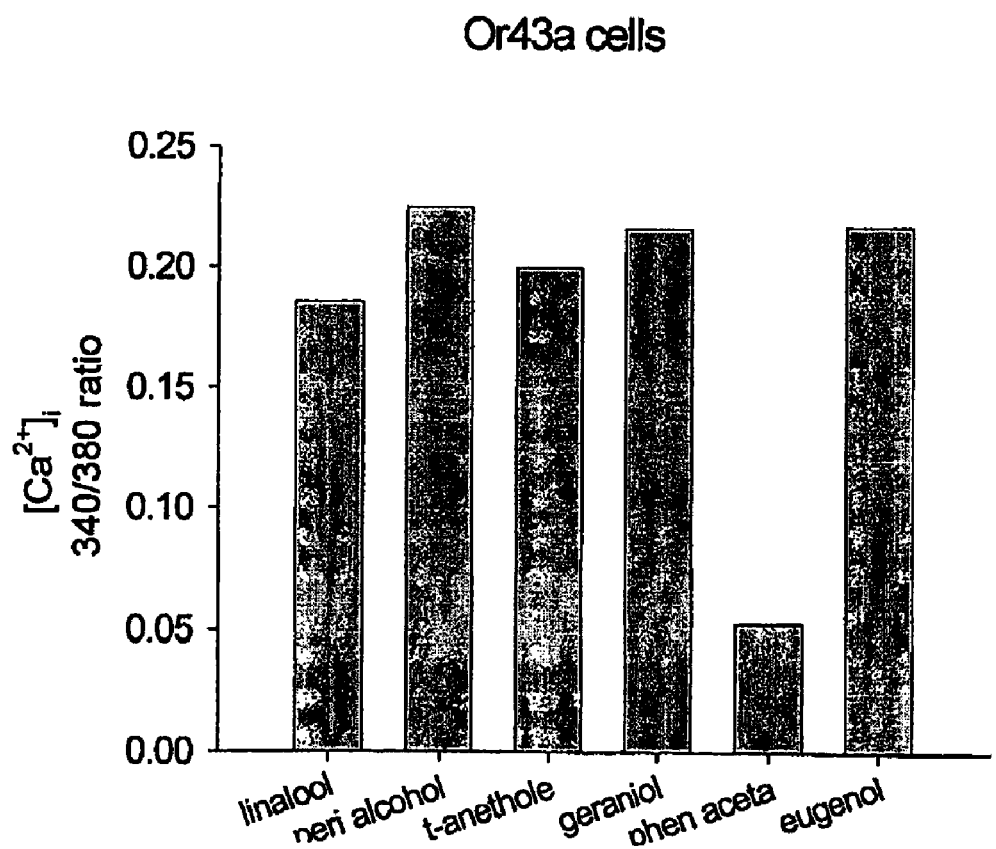
FIG. 23 shows the effect of linalool, perillyl alcohol, t-anethole, geraniol, phenyl acetaldehyde, and eugenol on intracellular $Ca^{2+}$ levels in Schneider cells expressing the Or43a receptor.

Effect of Various Plant Essential Oils on Intracellular Mobalization of $Ca^{2+}$ in Cells Expressing the Or43a Receptor To determine the effect of various plant essential oils on intracellular calcium mobilization, intact cells from each cell model are used in the assay as described above. Changes in intracellular $Ca^{2+}$ levels are calculated based on the difference between the 340/380 fluorescence ratios before and after approximately 150 seconds of the treatment. As shown in FIG. 22, treatment with ionomycin and tyramine, which induce mobilization of $Ca^{2+}$ in control cells, increases the intracellular $Ca^{2+}$ levels only negligibly in cells expressing the Or43a receptor.

Figure 24:
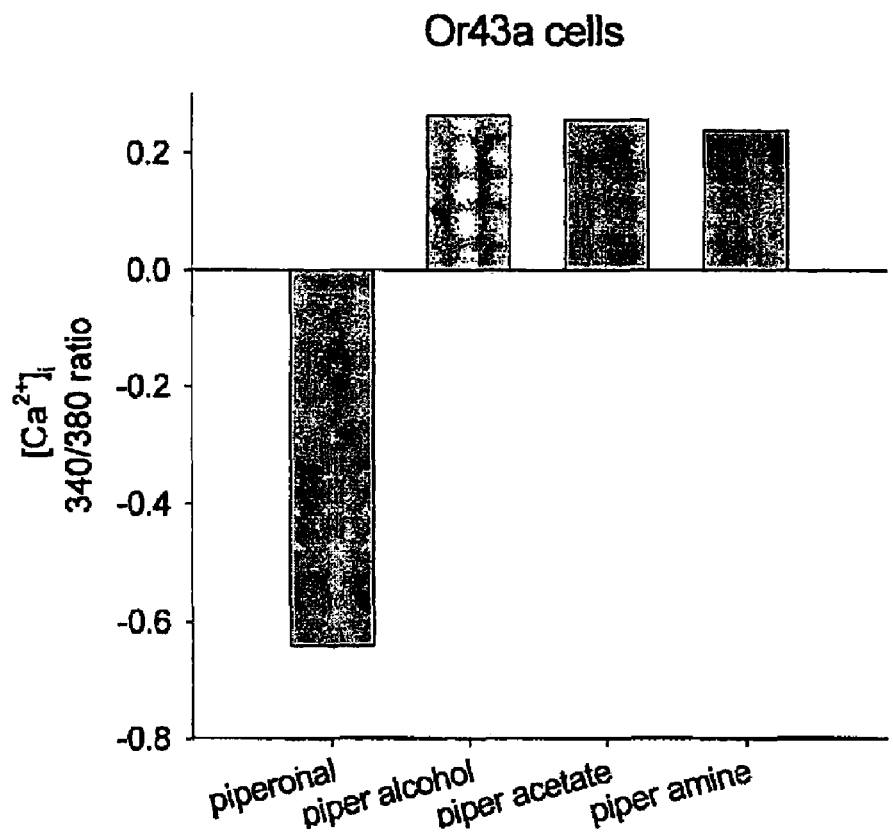
FIG. 24 shows the effect of piperonyl, piperonyl alcohol, piperonyl acetate, and piperonyl amine on intracellular $Ca^{2+}$ levels in Schneider cells expressing the Or43a receptor.
Figure 25:
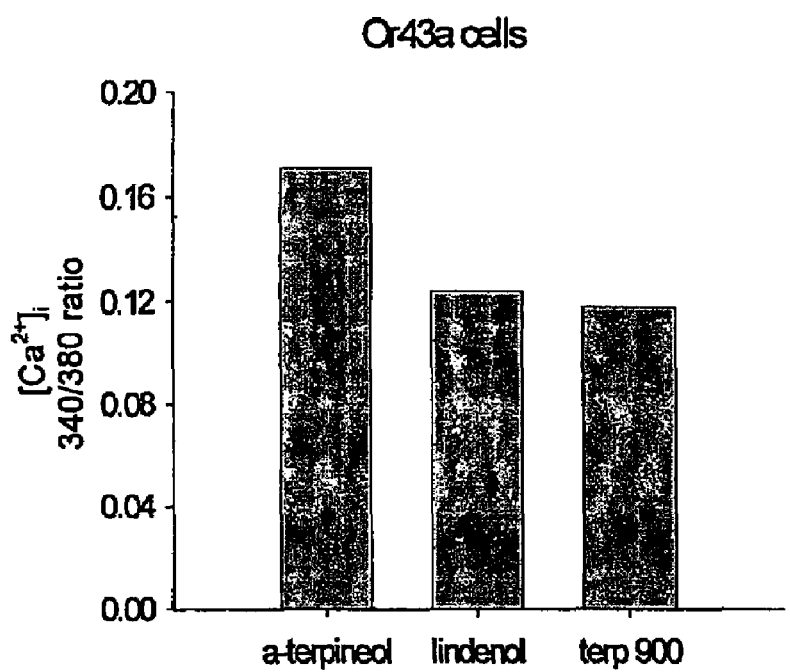
FIG. 25 shows the effect of α-termineol, lindenol, and terpinene 900 on intracellular $Ca^{2+}$ levels in Schneider cells expressing the Or43a receptor.
Figure 26:
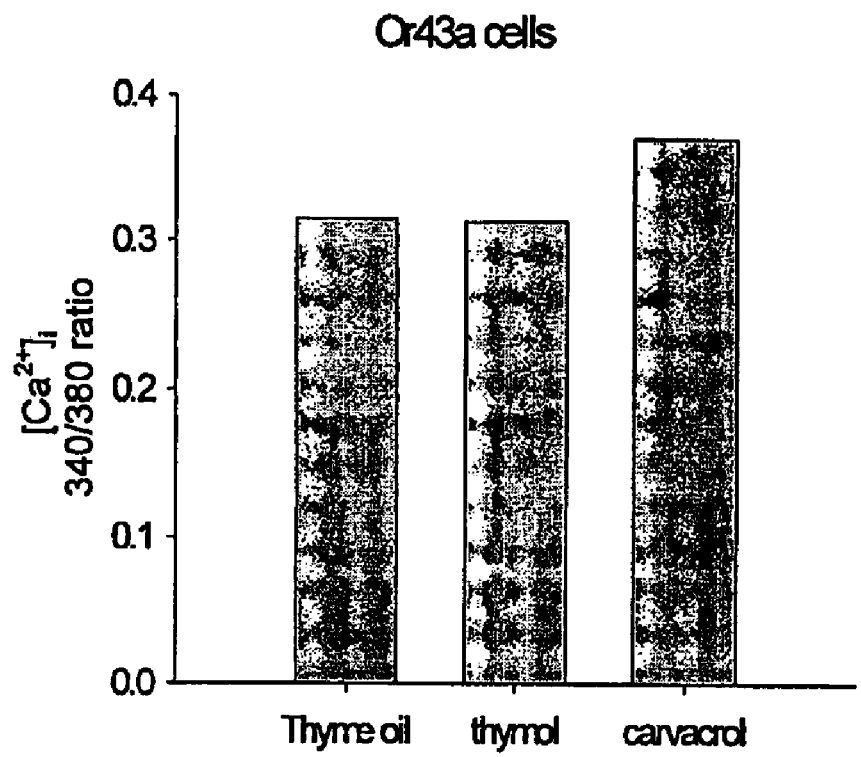
FIG. 26 shows the effect of thyme oil, thymol, and carvacrol on intracellular $Ca^{2+}$ levels in Schneider cells expressing the Or43a receptor.
Figure 27:
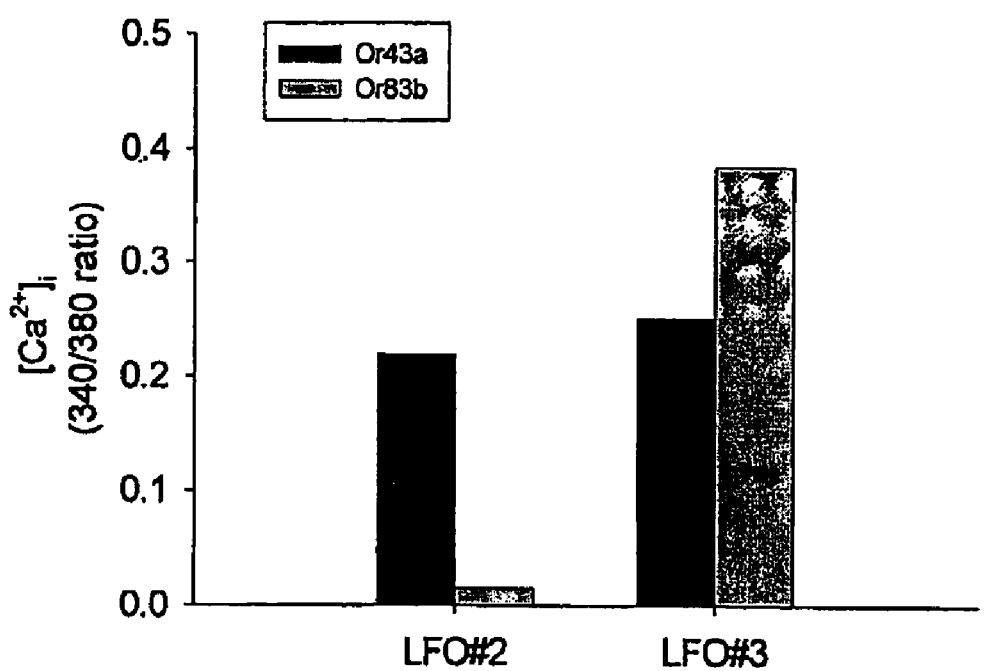
FIG. 27 shows the effect of LFO on intracellular $Ca^{2+}$ levels in Schneider cells expressing the Or43a receptor or the Or83b receptor.
Figure 28:
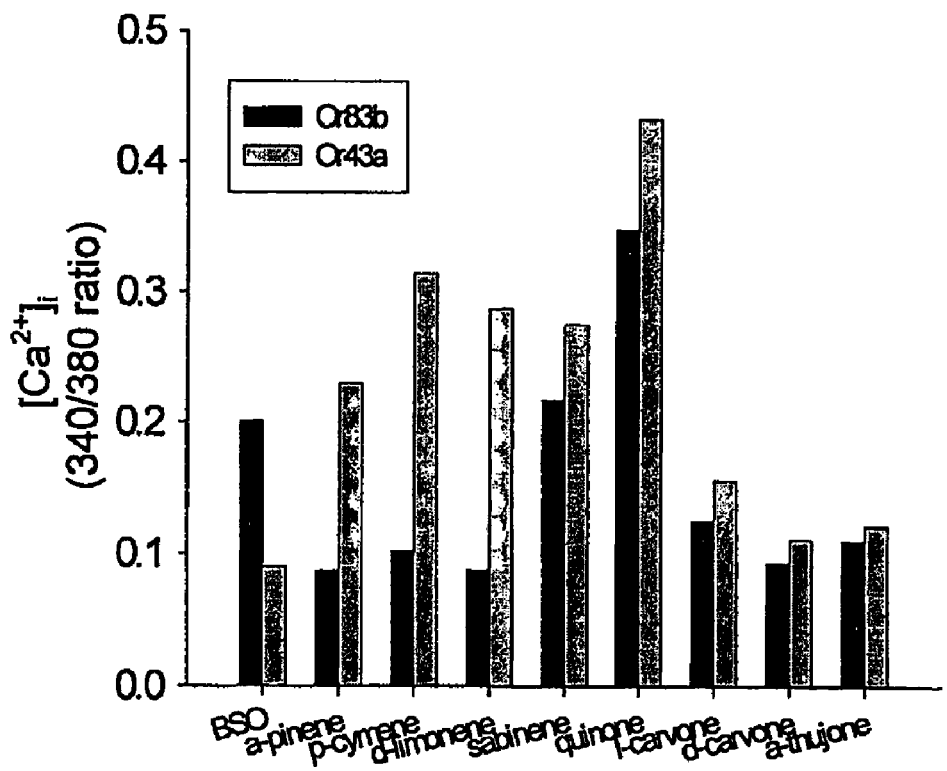
FIG. 28 shows the effect of BSO, α-pinene, p-cymene, d-limonene, sabinene, quinine, 1-carvone, d-carvone, and α-thujone on intracellular $Ca^{2+}$ levels in Schneider cells expressing the Or43a receptor or the Or83b receptor.

With reference to FIGS. 22 through 28, the following oils result in calcium mobilization in cells expressing the Or43a receptor: linalyl anthranilate, linalool, perillyl alcohol, t-anethole, geraniol, phenyl acetaldehyde, eugenol, piperonyl alcohol, piperonyl acetate, piperonyl amine, α-terpineol, lindenol, terpinene 900, thyme oil, thymol, carvacrol, LFO, BSO, α-pinene, p-cymene, d-limonene, sabinen, quinine, 1-carvone, d-carvone, and α-thujone. Finally, as shown in FIG. 24, treatment of piperonal decreases the intracellular $Ca^{2+}$ levels in cells expressing the Or43a receptor.

Treatment with certain other plant essential oils, including those expressly set forth in the application, also cause changes in intracellular $Ca^{2+}$ levels in cells expressing the Or43a receptor.

Additionally, treatment with certain other plant essential oils, including those expressly set forth in the application, cause changes in intracellular $Ca^{2+}$ levels in cells expressing the Or83b receptor.

EXAMPLE 11

Effect of Various Plant Essential Oils on cAMP Production in Cells Expressing Olfactory Receptors To determine the effect of various plant essential oils on intracellular cAMP production and the tyramine-dependent changes of cAMP in cells expressing one of the olfactory receptors, cells from each cell model are treated with LFO (about 50 μg/ml) and BSO (about 50 μg/ml) in the presence and absence of tyramine (about 20 μM) and forskolin (about 10 μM) and intracellular cAMP is thereafter quatified using the cAMP assay described above in Example 2.

Figure 29:
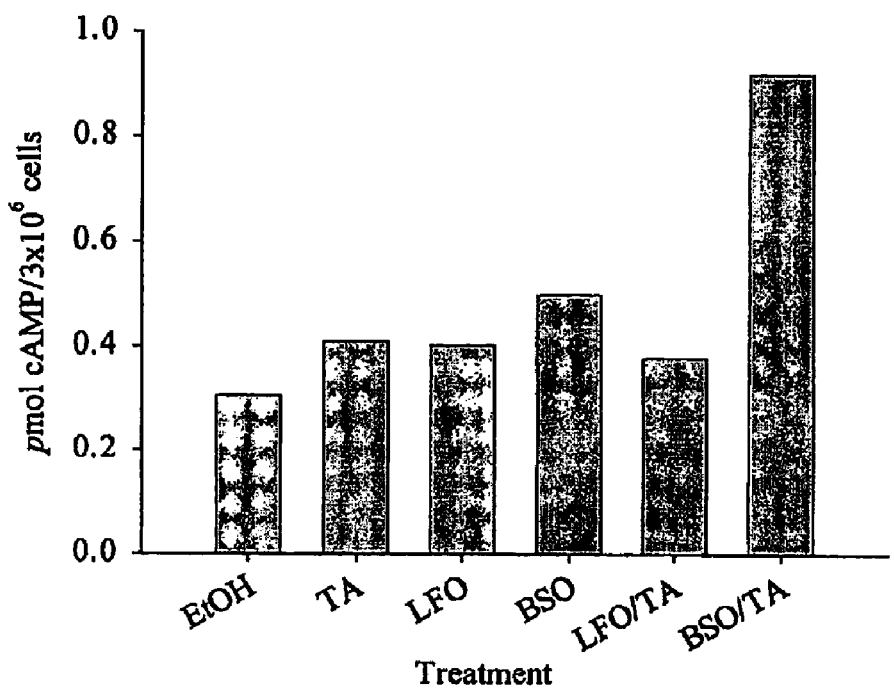
FIG. 29 shows tyramine dependent changes in cAMP levels in Schneider cells expressing Or83b receptor in the presence and absence of tyramine, LFO and BSO.
Figure 30:
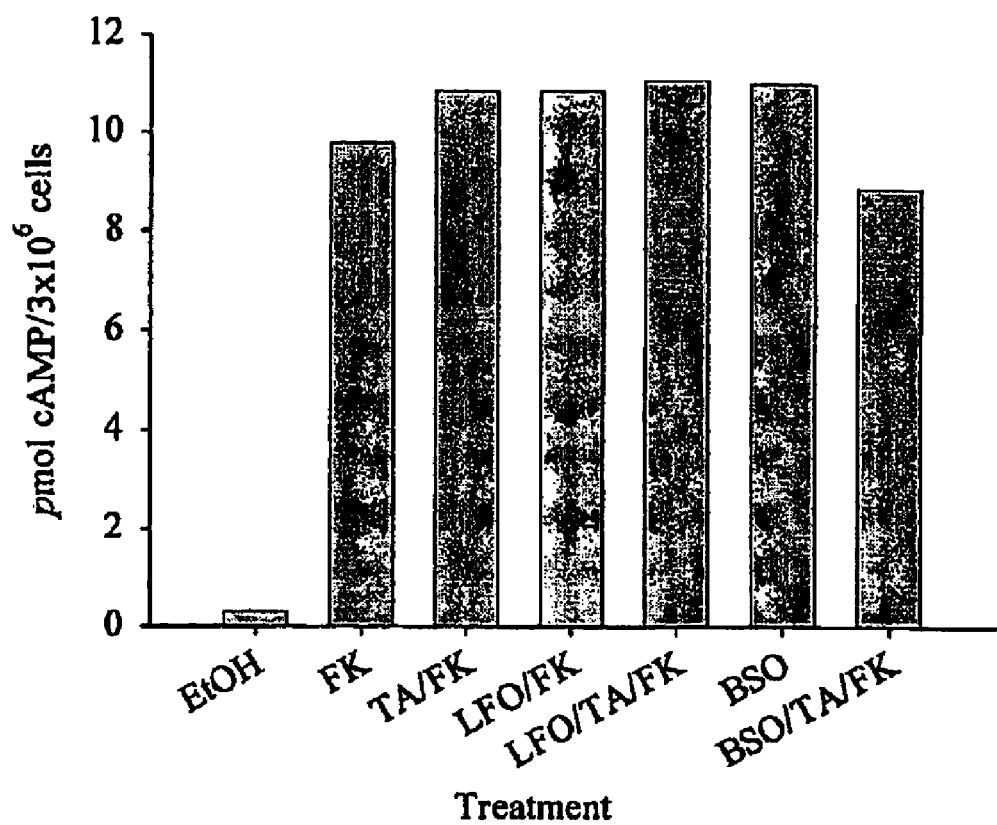
FIG. 30 shows the tyramine dependent changes in cAMP levels in Schneider cells expressing Or83b receptor treated with LFO and BSO in the presence and absence of tyramine and forskolin.

As shown in FIGS. 29 and 30, treatment with the following oils result in an increase in cAMP levels in cells expressing Or43a receptor: tyramine; LFO; BSO; LFO and tyramine; BSO and tyramine; forskolin; tyramine and forskolin; LFO and forskolin; LFO, forskolin and tyramine; BSO; and BSO, tyramine and forskolin.

Still referring to FIGS. 29 and 30, approximately 34%, 32% and 64% increases in cAMP production in cells expressing Or83b receptor are produced in response to treatment with about 20 μM tyramine, about 50 μg LFO/ml and about 50 μg BSO/ml, respectively. An antagonistic effect (about 24%) on cAMP production is found in response to co-treatment with tyramine and LFO, as compared to the effect of each one by itself. On the other hand, a synergistic effect (about 300% increases) of cAMP production is found in response to co-treatment with BSO and tyramine.

In the presence of forskolin (about 10 μM), approximately a 3000-fold increase in the production of cAMP is found. When forskolin-pretreated cells administered with either tyramine or LFO, only approximately a 10-13% increase of cAMP production is found beyond the effect of forskolin by itself. The addition of BSO to forskolin-pretreated cells induces about 22% more increase in the cAMP levels beyond the forskolin-induced cAMP production in these cells.

Additionally, treatment with certain other plant essential oils, including those expressly set forth in this application, result in changes in the intracellular cAMP levels in cells expressing either the Or43a or the Or83b receptor.

EXAMPLE 12

Toxicity of Compositions on *Drosophila Melanogaster* Fly

Two acetonic solutions (about 1% and 10%) from a test composition are prepared. Test concentration in acetone are then added to the inside of glass vials (about 5 mL) that are marked to about 3 cm above the bottom. The vials are rotated such that the inner surfaces of the vials, except the area between the marks to the neck, are left with a film of test composition. All vials are aerated for about 10 sec to ensure complete evaporation of acetone before introducing the flies to the treated vials. After complete evaporation of acetone, about 10 adult sex mixed flies are added to each vial and the vials are stoppered with cotton plugs. Mortality is observed about 24 hr after exposure.

EXAMPLE 13

Toxicity of Lilac Flower Oil (LFO) and Black Seed Oil (BSO) on Wild Type Fruit Fly and Tyramine-Receptor Mutant Fly Wild-type *Drosophila Melanogaster* (fruit fly) and tyramine-receptor mutant fruit fly are used as a model to determine the toxicity of LFO and BSO. The toxicity of these oils is studied using the method described above in Example 12. With reference to Tables C and D below, both chemicals are toxic to wild type fruit flies. LFO is about 300-fold more toxic to the fruit flies than BSO. The $LC_{50}$ for LFO is in the neighborhood of about 25-30 $ng/mm^2$ and the corresponding value for BSO is about 94 $\mu g/cm^2$. On the other hand, LFO is at least about 1000-fold less toxic against the tyramine receptor mutant fly than BSO. The toxicity of both chemicals against the fruit fly is mediated through the tyramine receptor. While the mutation of tyramine receptor significantly reduces LFO toxicity against the fruit fly, the same mutation develops a more susceptible strain of fruit fly to BSO.

TABLE C

| [LFO] | Wild/type flies | | [LFO] | Tyramine receptor mutant flies | |
|---|---|---|---|---|---|
| $ng/cm^2$ | Dead/alive | % mortality | $\mu g/cm^2$ | Dead/alive | % mortality |
| 10 | 0/30 | 0.00 | 20 | 0/30 | 0.00 |
| 15 | 8/30 | 26.66 | 24 | 0/30 | 0.00 |
| 20 | 10/30 | 33.33 | 26 | 5/30 | 16.66 |
| 25 | 13/30 | 43.33 | 30 | 11/30 | 36.66 |
| 30 | 18/30 | 60.00 | 35 | 22/30 | 73.33 |
| 35 | 25/30 | 83.33 | 38 | 28/30 | 93.33 |
| 40 | 30/30 | 100.00 | 40 | 30/30 | 100.00 |

TABLE D

| [BSO] | Wild/type flies | | [BSO] | Tyramine receptor mutant flies | |
|---|---|---|---|---|---|
| $\mu g/cm^2$ | Dead/alive | % mortality | $\mu g/cm^2$ | Dead/alive | % mortality |
| 18.90 | 0/30 | 00.00 | 18.90 | 5/20 | 25 |
| 37.74 | 3/30 | 10.00 | 37.74 | 8/20 | 40 |
| 56.60 | 8/30 | 26.66 | 56.60 | 15/20 | 75 |
| 94.34 | 15/30 | 50.00 | 94.34 | 18/20 | 90 |
| 141.51 | 21/30 | 70.00 | 141.51 | 20/20 | 100 |
| 188.68 | 30/30 | 100.00 | | | |

EXAMPLE 14

Repellent Effect of Compositions on Farm Ants

Adult insect are randomly selected for testing the repellent effect of compositions and are not individually marked. About 5 insects per replicate are used. About 3 replicates are used for each treatment. Untreated control tests are included with only solvent (acetone) application to an equal sized population/replications, held under identical conditions. A filter paper (about 80 $cm^2$) is treated with the composition (about 100 mg in 300 ml acetone). After about 3 min of air drying, the filter paper is placed in a dish and repellency against insects is performed. Insects are released to the dish, one insect at a time at the far end of the dish. Using one or more stopwatches, the time spent on either the filter paper or the untreated surface of the dish is recorded up to about 300 seconds. Repellency ratio (RR) is calculated as follows: RR= [(time on control surface−time on treated surface)/total time of test]. If RR >0 then the composition is considered to have a repellant effect, that is to say, an effect, wherein more insects are repelled away from treated surface than the control surface; if RR <0 then the composition is considered not to have a repellant effect.

EXAMPLE 15

Repellent Effect of Lilac Flower Oil (LFO) and Black Seed Oil (BSO) on Farm Ants The repellent effect of LFO (about 1.4 $mg/cm^2$) and BSO (about 1.4 $mg/cm^2$) against farm ants is studied using the method described above in Example 14. As shown in Tables E and F, BSO demonstrates more repellency against farm ants than LFO. Approximately 90% and 100% repellency against farm ants is provided by LFO and BSO, respectively. Additionally, LFO and BSO also induce 100% mortality against farm ants within 24 hr of exposure.

TABLE E

| Replicate number | Time on LFO test surface (sec) | | |
|---|---|---|---|
| | Treated surface | Untreated surface | Repellency % |
| R1 | 26.4 | 273.6 | 82.4 |
| R2 | 10.8 | 289.2 | 92.8 |
| R3 | 9.4 | 290.6 | 93.7 |
| X ± SD | 15.53 ± 7.7 | 284.47 ± 7.7 | 89.63 ± 5.1 |

TABLE F

| Replicate number | Time on BSO test surface (sec) | | |
|---|---|---|---|
| | Treated surface | Untreated surface | Repellency % |
| R1 | 0 | 300 | 100 |
| R2 | 0 | 300 | 100 |
| R3 | 0 | 300 | 100 |
| X ± SD | 0 ± 0 | 300 ± 0 | 100 ± 0 |

A dish treated with BSO is also used to address the residual effect of BSO on repellency against ants. Five ants are used per day according to the repellency protocol described above. In parallel, time-course toxicity for BSO is determined. In the toxicity experiment, an ant is exposed to the same treated surface for about 10 sec, and then transferred to a fresh container. Mortality data is recorded about 24 hr after exposure. Five ants are used per day. As shown in Table G, BSO provides repellency against farm ants up to about 4 days.

TABLE G

| Time elapsed after surface treatment, days | Repellency % |
|---|---|
| Day 1 | 100 |
| Day 2 | 100 |
| Day 3 | 100 |
| Day 4 | 100 |

EXAMPLE 16

Repellent Effect of d-Limonene, α-Pinene, and p-Cymene, Alone and in Combination, on Farm Ants The repellent effect of various plant essential oils is tested by treating a filter paper with the test oils. After about five minutes at room temperature, the paper is placed in a dish and ants are introduced one at a time. The repellency is determined as described above, in Example 14. Oils are tested alone. Additionally, oils are mixed to form compositions, which are then tested.

With reference to Table H, d-limonene, α-pinene, and p-cymene each demonstrate repellency alone. However, when the oils are mixed to form Composition A, a composition including about one third each of d-limonene, α-pinene and p-cymene, there is a synergistic effect and the percent repellency is greatly increased.

TABLE H

| | Repellency % | | | | | | | |
|---|---|---|---|---|---|---|---|---|
| | Day 0 | | Day 1 | | Day 2 | | Day 3 | |
| Test chemical | sec. on T surface | R % | sec. on T surface | R % | sec. on T surface | R % | sec. on T surface | R % |
| d-limonene | 55.7 | 62.9 | 136.2 | 27.6 | | | | |
| α-pinene | 77.4 | 48.4 | 139.2 | 07.2 | | | | |
| p-cymene | 86.2 | 42.5 | 133.6 | 10.9 | | | | |
| Composition A | 0.2 | 99.9 | 0.0 | 100.0 | 0.0 | 100 | | NO |

Likewise, and with reference to Table I, d-limonene and α-pinene each demonstrate repellency alone. However, when the oils are mixed to form Composition B, a composition including about half each d-limonene and α-pinene, there is a synergistic effect and the percent repellency is greatly increased.

TABLE I

| | Repellency % | | | | | | | |
|---|---|---|---|---|---|---|---|---|
| | Day 0 | | Day 1 | | Day 2 | | Day 3 | |
| Test chemical | sec. on T surface | R % | sec. on T surface | R % | sec. on T surface | R % | sec. on T surface | R % |
| d-limonene | 55.7 | 62.9 | 136.2 | 27.6 | | | | |
| α-pinene | 77.4 | 48.4 | 139.2 | 07.2 | | | | |
| Composition B | 1.0 | 99.3 | 1.0 | 99.3 | | NO | | |

EXAMPLE 17

Repellent Effect of Linalool, d-Limonene, α-Pinene, p-Cymene and Thyme Oil, Alone and in Combination, on Farm Ants The repellent effect of various plant essential oils is tested by treating a filter paper with the test oils. After about five minutes at room temperature, the paper is placed in a dish and ants are introduced one at a time. The repellency is determined as described above, in Example 14. Oils are tested alone. Additionally, oils are mixed to form compositions, which are then tested.

As shown in Table J, although d-limonene, α-pinene, p-cymene and thyme oil each display repellency, Composition C, a composition including about 25% of each of the oils, demonstrates repellency which exceed that of any of its component oils being used alone.

TABLE J

| | Repellency % | | | | | | | |
|---|---|---|---|---|---|---|---|---|
| | Day 0 | | Day 1 | | Day 2 | | Day 3 | |
| Test chemical | sec. on T surface | R % | sec. on T surface | R % | sec. on T surface | R % | sec. on T surface | R % |
| d-limonene | 55.7 | 62.9 | 136.2 | 27.6 | | | | |
| α-pinene | 77.4 | 48.4 | 139.2 | 07.2 | | | | |
| p-cymene | 86.2 | 42.5 | 133.6 | 10.9 | | | | |
| thyme oil | 58.0 | 61.3 | | | | | | |
| Composition C | 0.4 | 99.7 | 3.0 | 98.0 | 1.8 | 98.8 | 2.4 | 98.4 |

Likewise, as shown in Table K, although linalool, α-pinene, p-cymene and thyme oil each display repellency, Composition D, a composition including about 25% of each of the oils, demonstrates repellency which exceed that of any of its component oils being used alone.

TABLE K

| | Repellency % | | | | | | | |
|---|---|---|---|---|---|---|---|---|
| | Day 0 | | Day 1 | | Day 2 | | Day 3 | |
| Test chemical | sec. on T surface | R % | sec. on T surface | R % | sec. on T surface | R % | sec. on T surface | R % |
| linalool | 59.0 | 60.7 | 111.2 | 25.9 | | | | |
| α-pinene | 77.4 | 48.4 | 139.2 | 07.2 | | | | |
| p-cymene | 86.2 | 42.5 | 133.6 | 10.9 | | | | |
| thyme oil | 58.0 | 61.3 | | | | | | |
| Composition D | 8.2 | 97.3 | 3.0 | 98.0 | | | | |

Similarly, as shown in Table L, although linalool, α-pinene, and p-cymene each display repellency, Composition E, a composition including about one third of each of the oils, demonstrates repellency which exceed that of any of its component oils being used alone.

TABLE L

| | Repellency % | | | | | | | |
|---|---|---|---|---|---|---|---|---|
| | Day 0 | | Day 1 | | Day 2 | | Day 3 | |
| Test chemical | sec. on T surface | R % | sec. on T surface | R % | sec. on T surface | R % | sec. on T surface | R % |
| linalool | 59.0 | 60.7 | 111.2 | 25.9 | | | | |
| α-pinene | 77.4 | 48.4 | 139.2 | 07.2 | | | | |
| p-cymene | 86.2 | 42.5 | 133.6 | 10.9 | | | | |
| Composition E | 12.8 | 95.7 | 0.2 | 99.9 | 1.3 | 99.1 | 3.8 | 97.5 |

EXAMPLE 18

Repellent Effect of α-Pinene, Thyme Oil, α-Thujone, Sabinene, Alone and in Combination, on Farm Ants The repellent effect of various plant essential oils is tested by treating a filter paper with the test oils. After about five minutes at room temperature, the paper is placed in a dish and ants are introduced one at a time. The repellency is determined as described above, in Example 14. Oils are tested alone. Additionally, oils are mixed to form compositions, which are then tested.

Although α-pinene, thyme oil, α-thujone, and sabinene each display repellency, as shown in Table M, Composition F, a composition including about 25% of each of the oils, demonstrates enhanced repellency.

TABLE M

| | Repellency % | | | | | | | |
|---|---|---|---|---|---|---|---|---|
| | Day 0 | | Day 1 | | Day 2 | | Day 3 | |
| Test chemical | sec. on T surface | R % | sec. on T surface | R % | sec. on T surface | R % | sec. on T surface | R % |
| α-pinene | 77.4 | 48.4 | 139.2 | 07.2 | | | | |
| thyme oil | 58.0 | 61.3 | | | | | | |
| Composition F | 3.2 | 98.9 | 0.0 | 100.0 | 0.0 | 100.0 | 0.0 | 100.0 |

EXAMPLE 19

Repellent Effect of d-Limonene, p-Cymene, Thymol, Carvacrol and Geraniol, Alone and in Combination, on Farm Ants The repellent effect of various plant essential oils is tested by treating a filter paper with the test oils. After about five minutes at room temperature, the paper is placed in a dish and ants are introduced one at a time. The repellency is determined as described above, in Example 14. Oils are tested alone. Additionally, oils are mixed to form compositions, which are then tested.

As shown in Table N, although d-limonene, p-cymene, thymol and carvacrol each display repellency, Composition G, a composition including about 25% of each of the oils, demonstrates repellency which exceed that of any of its component oils being used alone.

TABLE N

| | Repellency % | | | | | | | |
|---|---|---|---|---|---|---|---|---|
| | Day 0 | | Day 1 | | Day 2 | | Day 3 | |
| Test chemical | sec. on T surface | R % | sec. on T surface | R % | sec. on T surface | R % | sec. on T surface | R % |
| d-limonene | 55.7 | 62.9 | 136.2 | 27.6 | | | | |
| p-cymene | 86.2 | 42.5 | 133.6 | 10.9 | | | | |
| thymol | 62.6 | 58.3 | 104.4 | 30.4 | | | | |
| carvacrol | | ND | | NO | | | | |
| Composition G | 2.5 | 99.2 | 7.6 | 94.9 | 0.0 | 100.0 | 4.0 | 94.0 |

Likewise, as shown in Table O, although d-limonene, p-cymene, and thymol each display repellency, Composition H, a composition including about one third of each of the oils, demonstrates repellency which exceed that of any of its component oils being used alone.

TABLE O

| | Repellency % | | | | | | | |
|---|---|---|---|---|---|---|---|---|
| | Day 0 | | Day 1 | | Day 2 | | Day 3 | |
| Test chemical | sec. on T surface | R % | sec. on T surface | R % | sec. on T surface | R % | sec. on T surface | R % |
| d-limonene | 55.7 | 62.9 | 136.2 | 27.6 | | | | |
| p-cymene | 86.2 | 42.5 | 133.6 | 10.9 | | | | |
| thymol | 62.6 | 58.3 | 104.4 | 30.4 | | | | |
| Composition H | 0.83 | 99.7 | 9.8 | 93.5 | 6.0 | 96 | 1.3 | 99.1 |

Similarly, as shown in Table P, although d-limonene, p-cymene, thymol, and geraniol each display repellency, Composition I, a composition including about 25% of each of the oils, demonstrates repellency which exceed that of any of its component oils being used alone.

TABLE P

| | Repellency % | | | | | | | |
|---|---|---|---|---|---|---|---|---|
| | Day 0 | | Day 1 | | Day 2 | | Day 3 | |
| Test chemical | sec. on T surface | R % | sec. on T surface | R % | sec. on T surface | R % | sec. on T surface | R % |
| d-limonene | 55.7 | 62.9 | 136.2 | 27.6 | | | | |
| p-cymene | 86.2 | 42.5 | 133.6 | 10.9 | | | | |
| thymol | 62.6 | 58.3 | 104.4 | 30.4 | | | | |
| geraniol | 69 | 54.0 | 129.0 | 14.0 | | | | |
| Composition I | 1.6 | 98.7 | 0.2 | 99.9 | 6.3 | 95.8 | 4.25 | 97.2 |

EXAMPLE 20

Repellent Effect of Linalyl Amthranilate, α-Pinene, d-Limonene, p-Cymene, and Geraniol, Alone and in Combination, on Farm Ants The repellent effect of various plant essential oils is tested by treating a filter paper with the test oils. After about five minutes at room temperature, the paper is placed in a dish and ants are introduced one at a time. The repellency is determined as described above, in Example 14. Oils are tested alone. Additionally, oils are mixed to form compositions, which are then tested.

As shown in Table Q, although geraniol, d-limonene, p-cymene and linalyl anthranilate each display repellency, Composition J, a composition including about 40% geraniol, about 30% d-limonene, about 10% p-cymene, about 10% α-pinene and about 10% linalyl anthranilate, demonstrates repellency which exceed that of any of its component oils being used alone.

TABLE Q

| Test chemical | Repellency % | | | | | | | |
|---|---|---|---|---|---|---|---|---|
| | Day 0 | | Day 1 | | Day 2 | | Day 3 | |
| | sec. on T surface | R % | sec. on T surface | R % | sec. on T surface | R % | sec. on T surface | R % |
| geraniol | 69.0 | 54.0 | 129.0 | 14.0 | | | | |
| d-limonene | 55.7 | 62.9 | 136.2 | 10.9 | | | | |
| α-pinene | 77.4 | 48.4 | 139.2 | 07.2 | | | | |
| p-cymene | 86.2 | 42.5 | 133.6 | 10.9 | | | | |
| linalyl anthranilate | 46.2 | 69.2 | 104.6 | 30.7 | | | | |
| Composition J | 0.0 | 100 | 0.0 | 100 | 0.2 | 99.9 | 0.0 | 100 |

EXAMPLE 21

Repellent Effect of d-Limonene, Thymol, α-Terpineol, Piperonyl Acetate, Piperonyl Amine, and Piperonal, Alone and in Combination, on Farm Ants The repellent effect of various plant essential oils is tested by treating a filter paper with the test oils. After about five minutes at room temperature, the paper is placed in a dish and ants are introduced one at a time. The repellency is determined as described above, in Example 14. Oils are tested alone. Additionally, oils are mixed to form compositions, which are then tested.

As shown in Table R, although d-limonene, thymol, α-terpineol, piperonyl acetate, piperonyl amine and piperonal each display repellency, Composition K, a composition including about 20% d-limonene, about 30% thymol, about 20% α-terpineol, about 10% piperonyl acetate, about 10% piperonyl amine and about 10% piperonal, demonstrates repellency which exceed that of any of its component oils being used alone.

TABLE R

| Test chemical | Repellency % | | | | | | | |
|---|---|---|---|---|---|---|---|---|
| | Day 0 | | Day 1 | | Day 2 | | Day 3 | |
| | sec. on T surface | R % | sec. on T surface | R % | sec. on T surface | R % | sec. on T surface | R % |
| d-limonene | 55.7 | 62.9 | 136.4 | 75.9 | | NO | | |
| thymol | 62.0 | 58.3 | 104.4 | 30.4 | | | | |
| α-terpineol | 109.6 | 26.9 | | | | | | |
| piperonyl-acetate | 52.4 | 65.1 | 106.6 | 28.9 | | | | |
| piperonylamine | 77.6 | 48.3 | 111.2 | 25.9 | | | | |
| piperonal | 93.6 | 37.6 | 125.8 | 16.1 | | | | |
| Composition K | 0.0 | 100 | 1.2 | 99.4 | 1.2 | 99.4 | 0.3 | 99.8 |

EXAMPLE 22

Repellent Effect of Geraniol, d-Limonene, Eugenol, Lindenol and Phenylacetaldehyde, Alone and in Combination, on Farm Ants The repellent effect of various plant essential oils is tested by treating a filter paper with the test oils. After about five minutes at room temperature, the paper is placed in a dish and ants are introduced one at a time. The repellency is determined as described above, in Example 14. Oils are tested alone. Additionally, oils are mixed to form compositions, which are then tested.

As shown in Table S, although geraniol, d-limonene, eugenol, lindenol, and phenylacetaldehyde each display repellency, Composition L, a composition including about 50% geraniol, about 20% d-limonene, about 10% eugenol, about 10% lindenol, and about 10% phenylacetaldehyde, demonstrates repellency which exceed that of any of its component oils being used alone.

TABLE S

| Test chemical | Repellency % | | | | | | | |
|---|---|---|---|---|---|---|---|---|
| | Day 0 | | Day 1 | | Day 2 | | Day 3 | |
| | sec. on T surface | R % | sec. on T surface | R % | sec. on T surface | R % | sec. on T surface | R % |
| geraniol | 69.0 | 54.0 | 129.4 | 14.0 | | | | |
| d-limonene | 55.7 | 62.9 | 133.6 | 10.9 | | | | |
| eugenol | 76.8 | 48.8 | 139.0 | 07.3 | | | | |
| lindenol | 144.2 | 04.0 | | | | | | |
| phenyl-acetaldehyde | 144.8 | 03.5 | | | | | | |
| Composition L | 0.0 | 100 | 0.0 | 100 | 0.2 | 99.9 | 0.0 | 100 |

EXAMPLE 23

Repellent Effect Geraniol, Lemon Grass Oil, Eugenol and Mineral Oil, Alone and in Combination, on Carpenter Ants The repellent effect of various plant essential oils is tested by treating a filter paper with the test oils. After about five minutes at room temperature, the paper is placed in a dish and ants are introduced one at a time. The repellency is determined as described above, in Example 14. Oils are tested alone. Additionally, oils are mixed to form compositions, which are then tested.

As shown in Table T, although geraniol, lemon grass oil and eugenol, each display repellency, Composition M, a composition including about 50% geraniol, about 40% lemon grass oil, and about 10% eugenol, demonstrates repellency which exceed that of any of its component oils being used alone. Geraniol, lemon grass oil and eugenol are all generally regarded as safe (GRAS compounds) by the Environmental Protection Agency (EPA) and the Food and Drug Administration (FDA), and, as such, are exempt from EPA pesticide registration requirements.

TABLE T

| Test chemical | Repellency % | | | | | | | |
|---|---|---|---|---|---|---|---|---|
| | Day 0 | | Day 1 | | Day 2 | | Day 3 | |
| | sec. on T surface | R % | sec. on T surface | R % | sec. on T surface | R % | sec. on T surface | R % |
| Geraniol | 69.0 | 129.0 | 129.0 | 14.0 | | | | |
| Lemongrass oil | 47.0 | 68.7 | 79.8 | 46.8 | | | | |
| eugenol | 76.8 | 48.8 | 139.0 | 7.3 | | | | |
| Composition M | 0.6 | 99.6 | 0.6 | 99.6 | 1.0 | 99.3 | 1.2 | 99.4 |

Likewise, as shown in Table U, although geraniol and lemon grass oil each display repellency, Composition N, a composition including about 70% geraniol and about 30% lemon grass oil, demonstrates repellency which exceed that of any of its component oils being used alone.

TABLE U

| | Repellency % | | | | | | |
|---|---|---|---|---|---|---|---|
| | Day 0 | | Day 1 | | Day 2 | | Day 3 |
| Test chemical | sec. on T surface | R % | sec. on T surface | R % | sec. on T surface | R % | sec. on T surface | R % |
| Geraniol | 69.0 | 54.0 | 129.0 | 14.0 | | | | |
| Lemongrass oil | 47.0 | 68.7 | 79.8 | 46.8 | | | | |
| Composition N | 0.67 | 99.6 | | | | | 0.80 | 99.5 |

Additionally, as shown in Table V, the addition of mineral oil, to form Composition O, a composition including about 60% geraniol, about 30% lemon grass oil, and about 10% mineral oil, does not effect the synergism of geraniol and lemongrass oil. Mineral oil alone does not demonstrate repellency, but serves to stabilize the composition, limiting the evaporation of the active components. Mineral oil, like geraniol and lemongrass oil, is a GRAS compound.

TABLE V

| | Repellency % | | | | | | |
|---|---|---|---|---|---|---|---|
| | Day 0 | | Day 1 | | Day 2 | | Day 3 |
| Test chemical | sec. on T surface | R % | sec. on T surface | R % | sec. on T surface | R % | sec. on T surface | R % |
| Geraniol | 69.0 | 54.0 | 129.0 | 14.0 | | | | |
| Lemongrass oil | 47.0 | 68.7 | 79.8 | 46.8 | | | | |
| Mineral oil | | NO | | | | | | |
| Composition O | 0.33 | 99.8 | | | 2.2 | 98.5 | 3.0 | 98.0 |

EXAMPLE 24

Repellent Effect Geraniol, Thymol, Lemon Grass Oil and Mineral Oil, Alone and in Combination, on Carpenter Ants The repellent effect of various plant essential oils is tested by treating a filter paper with the test oils. After about five minutes at room temperature, the paper is placed in a dish and ants are introduced one at a time. The repellency is determined as described above, in Example 14. Oils are tested alone. Additionally, oils are mixed to form compositions, which are then tested.

As shown in Table W, although geraniol, thymol and lemon grass oil, each display repellency, Composition P, a composition including about 50% geraniol, about 20% thymol, about 20% lemon grass oil, and about 10% mineral oil, demonstrates repellency which exceed that of any of its component oils being used alone. Geraniol, thymol, lemon grass oil, eugenol and mineral oil are all generally regarded as safe (GRAS compounds) by the Environmental Protection Agency (EPA) and the Food and Drug Administration (FDA), and, as such, are exempt from EPA pesticide registration requirements.

TABLE W

| | Repellency % | | | | | | |
|---|---|---|---|---|---|---|---|
| | Day 0 | | Day 1 | | Day 2 | | Day 3 |
| Test chemical | sec. on T surface | R % | sec. on T surface | R % | sec. on T surface | R % | sec. on T surface | R % |
| Geraniol | 69.0 | 54.0 | 129.0 | 14.0 | | | | |
| thymol | 62.0 | 58.3 | 104.4 | 30.4 | | | | |
| lemongrass oil | 47.0 | 68.7 | 79.8 | 46.8 | | | | |
| mineral oil | | NO | | | | | | |
| Composition P | 0.0 | 100 | 0.0 | 100 | 0.2 | 99.9 | 3.8 | 97.5 |

EXAMPLE 25

Repellent Effect Black Seed Oil (BSO), Lilac Flower Oil (LFO), Geraniol, Thymol, Lemon Grass Oil and Mineral Oil, Alone and in Combination, on Carpenter Ants The repellent effect of various plant essential oils is tested by treating a filter paper with the test oils. After about five minutes at room temperature, the paper is placed in a dish and ants are introduced one at a time. The repellency is determined as described above, in Example 14. Oils are tested alone. Additionally, oils are mixed to form compositions, which are then tested.

As shown in Table X, geraniol, thymol and thyme oil, each display repellency. As shown in Table Y, Compositions Q through V, containing various combinations of a BSO, LFO, geraniol, thymol, thyme oil, mineral oil, safflower oil and castor oil, demonstrate enhanced repellency.

TABLE X

| | Day 0 | |
|---|---|---|
| Test chemical | sec. on T surface | Repellency % |
| geraniol | 69 | 54.0 |
| thymol | 62 | 58.3 |
| thyme oil | 58 | 61.3 |
| mineral oil | | NO |
| safflower oil | | NO |
| castor oil | | NO |

TABLE Y

| | Day 0 | |
|---|---|---|
| Test chemicals | sec. on T surface | Repellency % |
| Composition Q about 25% geraniol and about 75% BSO | 0.2 | 99.9 |
| Composition R about 25% geraniol, about 50% BSO, and about 25% mineral oil | 1.0 | 99.3 |
| Composition S about 25% geraniol, about 50% BSO, and about 25% safflower oil | 1.0 | 99.3 |
| Composition T about 25% geraniol, about 25% thymol, and about 50% BSO | 1.6 | 98.9 |
| Composition U about 25% thyme oil, about 50% BSO, and about 25% castor oil | 2.3 | 98.5 |

TABLE Y-continued

| | Day 0 | |
|---|---|---|
| Test chemicals | sec. on T surface | Repellency % |
| Composition V about 50% geraniol and about 50% LFO | 0.4 | 99.7 |

EXAMPLE 26

Repellent Effect of Commercial Repellent 29% Deet on Carpenter Ants

For purposes of comparison to the repellent effect of various compositions made of various plant essential oils, the repellency of an insect control agent, the commercial repellent 29% DEET, which may be purchased under the name, REPEL® (Wisconsin Pharmacal Company, Inc, Jackson, Wyo.), is measured against Carpenter ants by treating a filter paper with the 29% DEET. After about five minutes at room temperature, the paper is placed in a dish and ants are introduced one at a time. The repellency is determined as described above, in Example 14. As shown in Table Z, 29% DEET has a percent repellency at day 0 of about 98.4 percent. The percent repellency of LFO, BSO, and the compositions of the present invention are comparable, and in some cases higher, than the percent repellency of 29% DEET.

TABLE Z

| | Repellency % Day 0 | |
|---|---|---|
| Test chemical | sec. on T surface | R % |
| DEET 29% | 02.4 | 98.4 |

EXAMPLE 27

Repellent Effect of Commercial Repellent Deet, Alone and in Combination with Geraniol, Thymol, and Lemon Grass Oil or Geranion, D-Limonene, Eugenol, Lindenol, and Phyenylacetaldehyde, on Carpenter Ants The repellent effect of commercial repellent DEET and various plant essential oils is tested by treating a filter paper with the test oils. After about five minutes at room temperature, the paper is placed in a dish and ants are introduced one at a time. The repellency is determined as described above, in Example 14. Oils are tested alone. Additionally, oils are mixed to form compositions, which are then tested.

As shown in Tables AA and BB, treatment with DEET in concentrations of about 5 to 10% displays no signs of repellency. However, as shown in Table AA, when combined with Composition W, a composition comprising about 25% geraniol, 10% thymol, 10% lemon grass oil and mineral oil (from 45 to 55% depending on the final concentration of DEET), percent repellency approaches 100. Likewise, as shown in Table BB, when combined with Composition X, a composition comprising about 25% geraniol, 10% d-limonene, 5% eugenol, 5% lindenol, 5% phenylacetaldehyde and mineral oil (from 40 to 50% depending on the final concentration of DEET), percent repellency is approximately 97 to 98 percent. Also, as shown in Tables AA and BB, enhanced repellency is shown when the various oils are combined with DEET.

TABLE AA

| | % Repellency | | | |
|---|---|---|---|---|
| | Day 0 | | Day 1 | |
| Chemicals | Sec on T | % Repellency | Sec on T | % Repellency |
| 5% DEET | 282 (10) | NO | | |
| 10% DEET | 260 (6) | NO | | |
| Composition W | 50 (6) | 67% | 174 (6) | NO |
| 5% DEET plus Composition W | 2.6 (1.9) | 98% | 10 (2) | 93% |
| 10% DEET plus Composition W | 0.2 (0.4) | 99% | 2.4 (1.8) | 98% |

TABLE BB

| | % Repellency | | | |
|---|---|---|---|---|
| | Day 0 | | Day 1 | |
| Chemicals | Sec on T | % Repellency | Sec on T | % Repellency |
| 5% DEET | 282 (10) | NO | | |
| 10% DEET | 260 (6) | NO | | |
| Composition X | 40 (5) | 74% | 145 (10) | 2 |
| 5% DEET plus Composition X | 4 (2) | 97% | 8.8 (4.0) | 94% |
| 10% DEET plus Composition X | 2.6 (2.0) | 98% | 7.2 (4.1) | 95% |

EXAMPLE 28

Pesticidal Effect of Compositions on Head Lice

Live adult head lice *Pediculus humanus capitus* are collected from female and male children between the age of about 4 and 11 living in the Karmos area, Alexandria, Egypt. The insects are collected using fine-toothed louse detector comb and pooled together. The collected lice are kept in dishes and used in the studies within about 30 minutes of their collection.

Various concentrations of the compositions being tested are prepared in water To allow the pesticidal effect of these compositions to be compared to that of a commercially available lice-killing agent, ivermectin, is dissolved in water. About 1 ml of each concentration of the compositions are applied to a dish, about 1 ml of the ivermectin solution is applied to a dish, and about 1 ml of water is applied to a control dish. About 10 adult head lice are introduced to each dish.

Treated and control dishes are kept under continuous observation and $LT_{100}$ is observed. LT refers to the time required to kill a given percentage of insects; thus, $LT_{100}$

EXAMPLE 29

Pesticidal Effect of Compositions Including Geramiol, D-Limonene, Benzyl Alcohol, P-Cymene, and Lilac Flower Oil on Head Lice The pesticidal effect of Composition Y, a composition including about 20% p-cymene, about 40% Lilac Flower Oil (LFO), about 30% benzyl alcohol, and about 10% mineral oil are studied using the method described above in Example 28. The $LT_{100}$ of this composition is compared to that of a commercially available lice-killing agent, ivermectin. As shown in Table CC, the lice treated with Composition Y are all killed more quickly than the lice treated with ivermectin.

TABLE CC

| Treatment | $LT_{100}$ (minutes) |
|---|---|
| Composition Y | 3 |
| Ivermectin | 5 |

EXAMPLE 30

Repellent Effect of Compositions To Mosouitoes

A. Oral Delivery

Hairless or shaved mice and guinea pigs are used to test the repellent effect of compositions delivered orally. The test oil (e.g., lilac flower oil (LFO) or black seed oil (BSO)) or test composition (e.g., a composition containing geraniol, d-linonene, eugenol, and lindenol) is administered orally to about 10 rodents. A control substance, such as mineral oil, is administered orally to about 10 rodents. After approximately 30 minutes, each rodent is placed in an enclosed container. About 20 mosquitoes are introduced to each container. Each container is observed for approximately 1 hour. The time that each insect spends on the rodent is recorded and number of lesions caused by the insect on the skin of the rodent is recorded. The insects spend less time on rodents receiving the test compositions than on the rodents receiving the control substance. The rodents receiving the test compositions receive fewer lesions than the rodents receiving the control substances.

B. Topical Delivery

Hairless or shaved mice and guinea pigs are used to test the repellent effect of compositions delivered topically. The test oil (e.g., lilac flower oil (LFO) or black seed oil (BSO)) or test composition (e.g., a composition containing geraniol, d-linonene, eugenol, and lindenol) is administered topically to the skin of about 10 rodents. A control substance, such as mineral oil, is administered topically to the skin of about 10 rodents. After approximately 30 minutes, each rodent is placed in an enclosed container. About 20 mosquitoes are introduced to each container. Each container is observed for approximately 1 hour. The time that each insect spends on the rodent is recorded and number of lesions caused by the insect on the skin of the rodent is recorded. The insects spend less time on rodents receiving the test compositions than on the rodents receiving the control substance. The rodents receiving the test compositions receive fewer lesions than the rodents receiving the control substances.

EXAMPLE 31

Repellent Effect of Compositions To Mosouitoes

About three cages are each stocked with about 100, southern house mosquitoes (*culex quinquefasciatus*), which are about 7 to 10 days-old. The mosquitoes are starved for about 12 hours. Each cage is supplied with four containers, each filled with cotton that has been soaked with sugar water.

Three of the four containers are treated randomly with about 1000 ppm (about 1 mg/l) of the composition being tested, while the remaining container serves as an untreated control. The containers are positioned in the four opposing corners of each cage and landing counts are conducted at about 0, 1, 2, 4, and 6 hour intervals following addition of the compositions being tested to the respective containers. The containers are removed from the cage between exposure intervals. Each exposure interval lasts for about 5 minutes.

The repellent effect of the compositions described in Table DD are tested using this method.

TABLE DD

| Composition | Ingredients (% expressed by weight) |
|---|---|
| EE | 10% DEET, 45% LFO, 45% cumin oil |
| AA | 50% geraniol, 40% thyme oil, 10% lemon grass oil |
| BB | 50% LFO, 50% cumin oil |

LFO, cumin oil, geraniol, thyme oil, and lemon grass oil are regarded as safe (GRAS compounds) by the Environmental Protection Agency (EPA) and the Food and Drug Administration (FDA), and, as such, are exempt from EPA pesticide registration requirements.

The landing counts are conducted at about 0, 1, 2, 4, and 6 hour intervals following addition of the compositions, set forth in Table DD, to the respective containers. The landing counts are set forth in Table EE. Percent repellency is calculated using this data and is expressed in Table FF. At each exposure interval, the Compositions EE, AA and BB display almost 100% repellency. Even after 6 hours, the Compositions display 100% repellency against mosquitoes.

TABLE EE

| | Landing Counts During Exposure Interval | | | | | |
|---|---|---|---|---|---|---|
| Exposure Time (hrs) | 0 | 1 | 2 | 4 | 6 | Total |
| Control | 36 | 26 | 30 | 13 | 6 | 111 |
| Composition EE | 0 | 1 | 1 | 0 | 0 | 2 |
| Composition AA | 0 | 0 | 0 | 1 | 0 | 1 |
| Composition BB | 0 | 0 | 0 | 0 | 0 | 0 |

TABLE FF

| | % Repellency ((control − composition)/control) × 100 | | | | |
|---|---|---|---|---|---|
| Exposure Time (hrs) | 0 | 1 | 2 | 4 | 6 |
| Composition EE | 100 | 96.2 | 96.7 | 100 | 100 |
| Composition AA | 100 | 100 | 100 | 92.3 | 100 |
| Composition BB | 100 | 100 | 100 | 100 | 100 |

EXAMPLE 32

Methods of Testing Repellent Effect and Pesticidal Effect of Compositions Containing Plant Essential Oils on Red Ants Pesticidal effect of various compositions containing plant essential oils on red ants is tested in the following manner. A paper disk is treated with about 20 µl of each of the composition being tested and the treated disks are each placed in a vial. An untreated paper disk is placed in a control vial. Also, a paper disk is treated with about 20 µl 100% DEET and placed in a vial to compare the pesticidal effect of the compositions to that of DEET, a known commercial insect control agent. About three red ants are introduced into each vial and the opening to the vials are closed with cotton to prevent the insects from escaping. The insect is exposed to the compositions for about one hour or less and mortality is recorded.

Repellent effect of various compositions containing plant essential oils on red ants is tested in the following manner. A paper disk is treated with about 200 µl of each composition and placed in a dish. An untreated paper disk is placed in a control dish. Also, a paper disk is treated with about 200 µl 100% DEET and placed in a dish to compare the repellant effect of the compositions to that of DEET. Red ants are introduced into each dish. Insect behavior and number of visits to the treated paper disk are monitored for about 5 minutes. The number of visits by a red ant to the paper disk is recorded.

Residuality, with regard to pesticidal effect and repellent effect, is tested by treating a paper disk with the composition being tested, keeping the treated paper disk under laboratory conditions for a predetermined period of time (e.g., 0 min, 6 hours, 1 day, 3 days, 5 days, 7 days), and exposing red ants to the treated paper disk in the above described manners.

EXAMPLE 33

Repellent Effect and Pesticidal Effect of Compositions Containing Plant Essential Oils on Red Ants The pesticidal effect and repellent effect of the compositions described in Table GG are tested using the methods described in Example 32. The untreated disks are neither toxic to nor do they repel red ants.

TABLE GG

| Composition | Ingredients (% expressed by weight) |
|---|---|
| Z | 20% d-limonene, 10% lindenol, 10% eugenol, 10% phenylacetaldehyde, 50% geraniol |
| AA | 50% geraniol, 40% thyme oil, 10% lemon grass oil |
| BB | 50% LFO, 50% cumin oil |
| CC | 20% d-limonene, 20% thyme oil, 20% geraniol, 20% a-pinene, 20% p-cymene |
| DD | 10% DEET, 18% d-limonene, 18% thyme oil, 18% geraniol, 18% a-pinene, 18% p-cymene |
| EE | 10% DEET, 45% LFO, 45% cumin oil |
| FF | 44% LFO 44% cumin oil, 10% geraniol, 2% thyme oil |

Each of the compositions results in 100% mortality, equivalent to that of DEET, when exposed to the paper disks about 0 min, 6 hours, 1 day, 3 days, 5 days, or 7 days after the paper disks are treated with the composition.

As shown in Table HH, red ants are repelled by the compositions used to treat the paper disks. Additionally, with regard to residuality, the compositions outperform DEET by retaining their potency for at least a week after being applied to the paper disks, while DEET begins to loose potency after 1 day. Table HH shows the number of trips by the red ants to the treated paper disks. The time periods set forth in the chart, 0 min, 6 hours, 1 day, 3 days, 5 days, or 7 days, refer to the approximate time elapsed between treatment of the paper disk with the composition and exposure of the red ants to the treated paper disk

TABLE HH

|  | 0 min | 6 hours | 1 day | 3 days | 5 days | 7 days |
|---|---|---|---|---|---|---|
| Composition Z | 0 | 0 | 0 | 0 | 0 | 0 |
| Composition AA | 0 | 0 | 0 | 0 | 0 | 0 |
| Composition BB | 0 | 0 | 0 | 0 | 0 | 0 |
| Composition CC | 0 | 0 | 0 | 0 | 0 | 0 |
| Composition DD | 0 | 0 | 0 | 0 | 0 | 0 |
| Composition EE | 0 | 0 | 0 | 0 | 0 | 0 |
| Composition FF | 0 | 0 | 0 | 0 | 0 | 1 |
| DEET (100%) | 0 | 0 | 1 | 2 | 2 | 2 |

EXAMPLE 34

Repellent Effect and Pesticidal Effect of Compositions Containing Plant Essential Oils on Red Ants The pesticidal effect and repellent effect of the compositions described in Table JJ were tested using the methods described in Example 32. Treatment with each of the compositions caused a repellent effect and a pesticidal effect.

TABLE JJ

| Composition | Ingredients (% expressed by weight) |
|---|---|
| GG | 10% d-limonene, 30% thyme oil, 35% geraniol, 10% a-pinene, 10% p-cymene, 5% phenylacetaldehyde |
| HH | 15% d-limonene, 50% geraniol, 15% a-pinene, 15% p-cymene, 5% phenylacetaldehyde |
| JJ | 50% d-limonene, 50% p-cymene |
| KK | 33.3% d-limonene, 33.3% p-cymene, 33.3% a-pinene |
| LL | 50% d-limonene, 50% thyme oil |
| MM | 50% thyme oil, 50% a-pinene |
| NN | 33.3% thyme oil, 33.3% a-pinene, 33.3% p-cymene |
| OO | 50% a-pinene, 50% p-cymene |
| PP | 25% linalool, 25% a-pinene, 25% p-cymene, 25% thyme oil |
| QQ | 33.3% linalool, 33.3% a-pinene, 33.3% p-cymene |
| RR | 33.3% d-limonene, 33.3% p-cymene, 33.3% thymol |
| SS | 25% d-limonene, 25% p-cymene, 25% thymol, 25% geraniol |

It will be apparent to those skilled in the art that various modifications and variations can be made in the present invention without departing from the scope or spirit of the invention. It is intended that the Specification and Example be considered as exemplary only, and not intended to limit the scope and spirit of the invention. The references and publications cited herein are incorporated herein by this reference.

Unless otherwise indicated, all numbers expressing quantities of ingredients, properties such as reaction conditions, and so forth used in the Specification, Examples, and Claims are to be understood as being modified in all instances by the term "about." Accordingly, unless indicated to the contrary, the numerical parameters set forth in the Specification, Example, and Claims are approximations that may vary depending upon the desired properties sought to be determined by the present invention.

What is claimed is:

1. A method of screening a composition for potential insect control activity, comprising:
   providing insect cells expressing olfactory receptor Or83b and a tyramine receptor;
   adding said composition to the cells;
   measuring the binding affinity of said composition to the receptor; and
   selecting a composition having an affinity for either of said receptors, wherein said affinity is indicative of potential insect control activity.

2. A method of screening a composition for potential insect control activity comprising:
   providing insect cells expressing olfactory receptor Or83b and a tyramine receptor;
   adding said composition to the cells;
   extracting intracellular cAMP or $Ca^{2+}$ from the cells;

measuring the intracellular cAMP or $Ca^{2+}$ levels;

comparing the intracellular cAMP or $Ca^{2+}$ levels in cells treated with said composition to the intracellular cAMP or $Ca^{2+}$ levels in untreated cells; and selecting a composition that causes a change in intracellular cAMP, $Ca^{2+}$, or both via at least one of said receptors, wherein said change is indicative of potential insect control activity.

3. The method of claim 2, wherein the tyramine receptor is expressed from the nucleic acid sequence as set for the in SEQ ID NO:1.

4. The method of claim 2, wherein the olfactory receptor Or83b is expressed from the nucleic acid sequence as set forth in SEQ ID NO:5.

5. The method of claim 2, wherein intracellular cAMP is extracted from the cells and its levels are measured and compared.

6. The method of claim 2, wherein intracellular $Ca^{2+}$ is extracted from the cells and its levels are measured and compared.

7. A method of screening a composition for potential insect control activity, comprising:

providing insect cells expressing olfactory receptor 83b and a tyramine receptor;

adding said composition to the cells;

measuring a characteristic of the cells in the presence of the composition, wherein the characteristic results from an interaction between the composition and at least one of the said receptors and is indicative of a potential for insect control activity; and selecting a composition suitable for insect control based on the results of the measuring step.

8. The method of claim 7, wherein the characteristic is selected from the group consisting of: a binding affinity of the composition to the receptor; a change in intracellular cAMP level; and a change in intracellular $Ca^{2+}$ level.

9. The method of claim 1, wherein the insect cells additionally express olfactory receptor 43a.

10. The method of claim 2, wherein the insect cells additionally express olfactory receptor 43a.

11. The method of claim 7, wherein the insect cells additionally express olfactory receptor 43a.

* * * * *

UNITED STATES PATENT AND TRADEMARK OFFICE
CERTIFICATE OF CORRECTION

PATENT NO. : 7,541,155 B2
APPLICATION NO. : 10/832022
DATED : June 2, 2009
INVENTOR(S) : Essam Enan It is certified that error appears in the above-identified patent and that said Letters Patent is hereby corrected as shown below:

Assignee on Cover Page; delete "Tyratech, Inc." and insert --TyraTech, Inc.--.
Column 9, line 22; delete "Schmeider" and insert --Schneider--.
Column 9, line 25; delete "Drosophika" and insert --Drosophila--.
Column 10, line 13; delete "C." and insert --C--.
Column 12, line 30; delete "Intracellulat" and insert --Intracellular--.
Column 12, lines 36, 47, 50 and 51; delete "C." and insert --C--.
Column 13, line 7; delete "Intracellulat" and insert --Intracellular--.
Column 19, line 4; delete "Wild Type" and insert --Wild-Type--.
Column 32, line 3; delete "Mosouitoes" and insert --Mosquitoes--.

Signed and Sealed this

First Day of December, 2009

David J. Kappos
*Director of the United States Patent and Trademark Office*

SEQUENCE LISTING

<160> NUMBER OF SEQ ID NOS: 12

<210> SEQ ID NO 1
<211> LENGTH: 1806
<212> TYPE: DNA
<213> ORGANISM: Drosophila melanogaster

<400> SEQUENCE: 1

| | | | | | | |
|---|---|---|---|---|---|---|
| atgccatcgg | cagatcagat | cctgtttgta | aatgtcacca | caacggtggc | ggcggcggct | 60 |
| ctaaccgctg | cggccgccgt | cagcaccaca | aagtccggaa | gcggcaacgc | cgcacggggc | 120 |
| tacacggatt | cggatgacga | tgcgggcatg | ggaacggagg | cggtggctaa | catatccggc | 180 |
| tcgctggtgg | agggcctgac | caccgttacc | gcggcattga | gtacggctca | ggcggacaag | 240 |
| gactcagcgg | gagaatgcga | aggagctgtg | gaggagctgc | atgccagcat | cctgggcctc | 300 |
| cagctggctg | tgccggagtg | ggaggccctt | ctcaccgccc | tggttctctc | ggtcattatc | 360 |
| gtgctgacca | tcatcgggaa | catcctggtg | attctgagtg | tgttcaccta | caagccgctg | 420 |
| cgcatcgtcc | agaacttctt | catagtttcg | ctggcggtgg | ccgatctcac | ggtggccctt | 480 |
| ctggtgctgc | ccttcaacgt | ggcttactcg | atcctggggc | gctgggagtt | cggcatccac | 540 |
| ctgtgcaagc | tgtggctcac | ctgcgacgtg | ctgtgctgca | ctagctccat | cctgaacctg | 600 |
| tgtgccatag | ccctcgaccg | gtactgggcc | attacggacc | ccatcaacta | tgcccagaag | 660 |
| aggaccgttg | gtcgcgtcct | gctcctcatc | tccggggtgt | ggctactttc | gctgctgata | 720 |
| agtagtccgc | cgttgatcgg | ctggaacgac | tggccggacg | agttcacaag | cgccacgccc | 780 |
| tgcgagctga | cctcgcagcg | aggctacgtg | atctactcct | cgctgggctc | cttctttatt | 840 |
| ccgctggcca | tcatgacgat | cgtctacatc | gagatcttcg | tggccacgcg | cgccgccta | 900 |
| agggagcgag | ccagggccaa | caagcttaac | acgatcgctc | tgaagtccac | tgagctcgag | 960 |
| ccgatggcaa | actcctcgcc | cgtcgccgcc | tccaactccg | gctccaagtc | gcgtctccta | 1020 |
| gccagctggc | tttgctgcgg | ccgggatcgg | gcccagttcg | ccacgcctat | gatccagaac | 1080 |
| gaccaggaga | gcatcagcag | tgaaacccac | cagccgcagg | attcctccaa | agcgggtccc | 1140 |
| catggcaaca | gcgatccccca | acagcagcac | gtggtcgtgc | tggtcaagaa | gtcgcgtcgc | 1200 |
| gccaagacca | aggactccat | taagcacggc | aagacccgtg | gtggccgcaa | gtcgcagtcc | 1260 |
| tcgtccacat | gcgagcccca | cggcgagcaa | cagctcttac | ccgccggcgg | ggatggcggt | 1320 |
| agctgccagc | ccggcggagg | ccactctgga | ggcggaaagt | cggacgccga | gatcagcacg | 1380 |
| gagagcggga | gcgatcccaa | aggttgcata | caggtctgcg | tgactcaggc | ggacgagcaa | 1440 |
| acgtccctaa | agctgacccc | gccgcaatcc | tcgacgggga | tcgctgccgt | ttctgtcact | 1500 |
| ccgttgcaga | agaagactag | tggggttaac | cagttcattg | aggagaaaca | gaagatctcg | 1560 |
| ctttccaagg | agcggcgagc | ggctcgcacc | ctgggcatca | tcatgggcgt | gttcgtcatc | 1620 |
| tgctggctgc | ccttcttcct | catgtacgtc | attctgccct | ctgccagac | ctgctgcccc | 1680 |
| acgaacaagt | tcaagaactt | catcacctgg | ctgggctaca | tcaactcggg | cctgaatccg | 1740 |
| gtcatctaca | ccatcttcaa | cctggactac | cgccgggcct | tcaagcgact | tctgggcctg | 1800 |
| aattga | | | | | | 1806 |

<210> SEQ ID NO 2
<211> LENGTH: 601
<212> TYPE: PRT
<213> ORGANISM: Drosophila melanogaster

```
<400> SEQUENCE: 2

Met Pro Ser Ala Asp Gln Ile Leu Phe Val Asn Val Thr Thr Thr Val
1               5                   10                  15

Ala Ala Ala Ala Leu Thr Ala Ala Ala Val Ser Thr Thr Lys Ser
            20                  25                  30

Gly Ser Gly Asn Ala Ala Arg Gly Tyr Thr Asp Ser Asp Asp Ala
            35                  40                  45

Gly Met Gly Thr Glu Ala Val Ala Asn Ile Ser Gly Ser Leu Val Glu
50                  55                  60

Gly Leu Thr Thr Val Thr Ala Ala Leu Ser Thr Ala Gln Ala Asp Lys
65                  70                  75                  80

Asp Ser Ala Gly Glu Cys Glu Gly Ala Val Glu Glu Leu His Ala Ser
                85                  90                  95

Ile Leu Gly Leu Gln Leu Ala Val Pro Glu Trp Glu Ala Leu Leu Thr
            100                 105                 110

Ala Leu Val Leu Ser Val Ile Ile Val Leu Thr Ile Ile Gly Asn Ile
            115                 120                 125

Leu Val Ile Leu Ser Val Phe Thr Tyr Lys Pro Leu Arg Ile Val Gln
130                 135                 140

Asn Phe Phe Ile Val Ser Leu Ala Val Ala Asp Leu Thr Val Ala Leu
145                 150                 155                 160

Leu Val Leu Pro Phe Asn Val Ala Tyr Ser Ile Leu Gly Arg Trp Glu
            165                 170                 175

Phe Gly Ile His Leu Cys Lys Leu Trp Leu Thr Cys Asp Val Leu Cys
            180                 185                 190

Cys Thr Ser Ser Ile Leu Asn Leu Cys Ala Ile Ala Leu Asp Arg Tyr
            195                 200                 205

Trp Ala Ile Thr Asp Pro Ile Asn Tyr Ala Gln Lys Arg Thr Val Gly
210                 215                 220

Arg Val Leu Leu Leu Ile Ser Gly Val Trp Leu Leu Ser Leu Leu Ile
225                 230                 235                 240

Ser Ser Pro Pro Leu Ile Gly Trp Asn Asp Trp Pro Asp Glu Phe Thr
            245                 250                 255

Ser Ala Thr Pro Cys Glu Leu Thr Ser Gln Arg Gly Tyr Val Ile Tyr
            260                 265                 270

Ser Ser Leu Gly Ser Phe Phe Ile Pro Leu Ala Ile Met Thr Ile Val
            275                 280                 285

Tyr Ile Glu Ile Phe Val Ala Thr Arg Arg Arg Leu Arg Glu Arg Ala
290                 295                 300

Arg Ala Asn Lys Leu Asn Thr Ile Ala Leu Lys Ser Thr Glu Leu Glu
305                 310                 315                 320

Pro Met Ala Asn Ser Ser Pro Val Ala Ala Ser Asn Ser Gly Ser Lys
            325                 330                 335

Ser Arg Leu Leu Ala Ser Trp Leu Cys Cys Gly Arg Asp Arg Ala Gln
            340                 345                 350

Phe Ala Thr Pro Met Ile Gln Asn Asp Gln Glu Ser Ile Ser Ser Glu
            355                 360                 365

Thr His Gln Pro Gln Asp Ser Ser Lys Ala Gly Pro His Gly Asn Ser
            370                 375                 380

Asp Pro Gln Gln Gln His Val Val Leu Val Lys Lys Ser Arg Arg
385                 390                 395                 400

Ala Lys Thr Lys Asp Ser Ile Lys His Gly Lys Thr Arg Gly Gly Arg
```

```
                    405                 410                 415
Lys Ser Gln Ser Ser Ser Thr Cys Glu Pro His Gly Glu Gln Gln Leu
            420                 425                 430
Leu Pro Ala Gly Gly Asp Gly Gly Ser Cys Gln Pro Gly Gly His
            435                 440                 445
Ser Gly Gly Gly Lys Ser Asp Ala Glu Ile Ser Thr Glu Ser Gly Ser
        450                 455                 460
Asp Pro Lys Gly Cys Ile Gln Val Cys Val Thr Gln Ala Asp Glu Gln
465                 470                 475                 480
Thr Ser Leu Lys Leu Thr Pro Pro Gln Ser Ser Thr Gly Val Ala Ala
                485                 490                 495
Val Ser Val Thr Pro Leu Gln Lys Lys Thr Ser Gly Val Asn Gln Phe
            500                 505                 510
Ile Glu Glu Lys Gln Lys Ile Ser Leu Ser Lys Glu Arg Arg Ala Ala
            515                 520                 525
Arg Thr Leu Gly Ile Ile Met Gly Val Phe Val Ile Cys Trp Leu Pro
        530                 535                 540
Phe Phe Leu Met Tyr Val Ile Leu Pro Phe Cys Gln Thr Cys Cys Pro
545                 550                 555                 560
Thr Asn Lys Phe Lys Asn Phe Ile Thr Trp Leu Gly Tyr Ile Asn Ser
                565                 570                 575
Gly Leu Asn Pro Val Ile Tyr Thr Ile Phe Asn Leu Asp Tyr Arg Arg
                580                 585                 590
Ala Phe Lys Arg Leu Leu Gly Leu Asn
            595                 600

<210> SEQ ID NO 3
<211> LENGTH: 1128
<212> TYPE: DNA
<213> ORGANISM: Drosophila melanogaster

<400> SEQUENCE: 3
atgacaatcg aggatatcgg cctggtgggc atcaacgtgc ggatgtggcg acacttggcc    60
gtgctgtacc ccactccggg ctccagctgg cgcaagttcg ccttcgtact gccggtgact   120
gcgatgaatc tgatgcagtt cgtctacctg ctgcggatgt ggggcgacct gcccgccttc   180
attctgaaca tgttcttctt ctcggccatt ttcaacgccc tgatgcgcac gtggctggtc   240
ataatcaagc ggcgccagtt cgaggagttt ctcggccaac tggccactct gttccattcg   300
attctcgact ccaccgacga gtggggcgt ggcatcctgc ggagggcgga acggaggct    360 cggaacctgg ccatccttaa tttgagtgcc tccttcctgg acattgtcgg tgctctggta   420
tcgccgcttt caggggagga gagagctcat cccttcggcg tagctctacc aggagtgagc   480
atgaccagtt cgcctgtcta cgaggttatc tacttggccc aactgcctac gcccctgctg   540
ctgtccatga tgtacatgcc tttcgtcagc ctttttgccg gctggccat ctttgggaag   600 gccatgctgc agatcctggt acacaggctg ggccagattg cggagaaga gcagtcggag   660 gaggagcgct tccaaaggct ggcctcctgc attgcgtacc acacgcaggt gatgcgctat   720
gtgtggcagc tcaacaaact ggtggccaac attgtggcgg tggaagcaat tattttttggc   780 tcgataatct gctcactgct cttctgtctg aatattataa cctcacccac ccaggtgatc   840
tcgatagtga tgtacattct gaccatgctg tacgttctct tcacctacta caatcgggcc   900
aatgaaatat gcctcgagaa caaccggggtg gcggaggctg tttacaatgt gcccggtac   960 gaggcaggaa ctcggttcg caaaaccctc ctgatcttct tgatgcaaac acaacacccg   1020
```

-continued

```
atggagataa gagtcggcaa cgtttacccc atgacattgg ccatgttcca gagtctgttg   1080
aatgcgtcct actcctactt taccatgctg cgtggcgtca ccggcaaa              1128
```

<210> SEQ ID NO 4
<211> LENGTH: 376
<212> TYPE: PRT
<213> ORGANISM: Drosophila melanogaster

<400> SEQUENCE: 4

| Met | Thr | Ile | Glu | Asp | Ile | Gly | Leu | Val | Gly | Ile | Asn | Val | Arg | Met | Trp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Arg His Leu Ala Val Leu Tyr Pro Thr Pro Gly Ser Ser Trp Arg Lys
            20                  25                  30

Phe Ala Phe Val Leu Pro Val Thr Ala Met Asn Leu Met Gln Phe Val
        35                  40                  45

Tyr Leu Leu Arg Met Trp Gly Asp Leu Pro Ala Phe Ile Leu Asn Met
    50                  55                  60

Phe Phe Phe Ser Ala Ile Phe Asn Ala Leu Met Arg Thr Trp Leu Val
65                  70                  75                  80

Ile Ile Lys Arg Arg Gln Phe Glu Glu Phe Leu Gly Gln Leu Ala Thr
                85                  90                  95

Leu Phe His Ser Ile Leu Asp Ser Thr Asp Glu Trp Gly Arg Gly Ile
            100                 105                 110

Leu Arg Arg Ala Glu Arg Glu Ala Arg Asn Leu Ala Ile Leu Asn Leu
        115                 120                 125

Ser Ala Ser Phe Leu Asp Ile Val Gly Ala Leu Val Ser Pro Leu Phe
    130                 135                 140

Arg Glu Glu Arg Ala His Pro Phe Gly Val Ala Leu Pro Gly Val Ser
145                 150                 155                 160

Met Thr Ser Ser Pro Val Tyr Glu Val Ile Tyr Leu Ala Gln Leu Pro
                165                 170                 175

Thr Pro Leu Leu Leu Ser Met Met Tyr Met Pro Phe Val Ser Leu Phe
            180                 185                 190

Ala Gly Leu Ala Ile Phe Gly Lys Ala Met Leu Gln Ile Leu Val His
        195                 200                 205

Arg Leu Gly Gln Ile Gly Gly Glu Glu Gln Ser Glu Glu Arg Phe
    210                 215                 220

Gln Arg Leu Ala Ser Cys Ile Ala Tyr His Thr Gln Val Met Arg Tyr
225                 230                 235                 240

Val Trp Gln Leu Asn Lys Leu Val Ala Asn Ile Val Ala Val Glu Ala
                245                 250                 255

Ile Ile Phe Gly Ser Ile Ile Cys Ser Leu Leu Phe Cys Leu Asn Ile
            260                 265                 270

Ile Thr Ser Pro Thr Gln Val Ile Ser Ile Val Met Tyr Ile Leu Thr
        275                 280                 285

Met Leu Tyr Val Leu Phe Thr Tyr Tyr Asn Arg Ala Asn Glu Ile Cys
    290                 295                 300

Leu Glu Asn Asn Arg Val Ala Glu Ala Val Tyr Asn Val Pro Trp Tyr
305                 310                 315                 320

Glu Ala Gly Thr Arg Phe Arg Lys Thr Leu Leu Ile Phe Leu Met Gln
                325                 330                 335

Thr Gln His Pro Met Glu Ile Arg Val Gly Asn Val Tyr Pro Met Thr
            340                 345                 350

Leu Ala Met Phe Gln Ser Leu Leu Asn Ala Ser Tyr Ser Tyr Phe Thr
        355                 360                 365

Met Leu Arg Gly Val Thr Gly Lys
    370                 375

<210> SEQ ID NO 5
<211> LENGTH: 1461
<212> TYPE: DNA
<213> ORGANISM: Drosophila melanogaster

<400> SEQUENCE: 5

| | | | | | | |
|---|---|---|---|---|---|---|
| atgacaacct | cgatgcagcc | gagcaagtac | acgggcctgg | tcgccgacct | gatgcccaac | 60 |
| atccgggcga | tgaagtactc | cggcctgttc | atgcacaact | tcacgggcgg | cagtgccttc | 120 |
| atgaagaagg | tgtactcctc | cgtgcacctg | gtgttcctcc | tcatgcagtt | cacccttcatc | 180 |
| ctggtcaaca | tggccctgaa | cgccgaggag | gtcaacgagc | tgtcgggcaa | cacgatcacg | 240 |
| accctcttct | tcacccactg | catcacgaag | tttatctacc | tggctgttaa | ccagaagaat | 300 |
| ttctacagaa | cattgaatat | atggaaccag | gtgaacacgc | atcccttgtt | cgccgagtcg | 360 |
| gatgctcgtt | accattcgat | cgcactggcg | aagatgagga | agctgttctt | tctggtgatg | 420 |
| ctgaccacag | tcgcctcggc | caccgcctgg | accacgatca | ccttctttgg | cgacagcgta | 480 |
| aaaatggtgg | tggaccatga | gacgaactcc | agcatcccgg | tggagatacc | ccggctgccg | 540 |
| attaagtcct | tctacccgtg | gaacgccagc | cacggcatgt | tctacatgat | cagctttgcc | 600 |
| tttcagatct | actacgtgct | cttctcgatg | atccactcca | atctatgcga | cgtgatgttc | 660 |
| tgctcttggc | tgatattcgc | ctgcgagcag | ctgcagcact | tgaagggcat | catgaagccg | 720 |
| ctgatggagc | tgtccgcctc | gctggacacc | tacaggccca | actcggcggc | cctcttcagg | 780 |
| tccctgtcgg | ccaactccaa | gtcggagcta | attcataatg | aagaaaagga | tcccggcacc | 840 |
| gacatggaca | tgtcgggcat | ctacagctcg | aaagcggatt | ggggcgctca | gtttcgagca | 900 |
| ccctcgacac | tgcagtcctt | tggcgggaac | ggggcggag | gcaacgggtt | ggtgaacggc | 960 |
| gctaatccca | acgggctgac | caaaaagcag | gagatgatgg | tgcgcagtgc | catcaagtac | 1020 |
| tgggtcgagc | ggcacaagca | cgtggtgcga | ctggtggctg | ccatcggcga | tacttacgga | 1080 |
| gccgccctcc | tcctccacat | gctgacctcg | accatcaagc | tgaccctgct | ggcataccag | 1140 |
| gccaccaaaa | tcaacggagt | gaatgtctac | gccttcacag | tcgtcggata | cctaggatac | 1200 |
| gcgctggccc | aggtgttcca | cttttgcatc | tttggcaatc | gtctgattga | agagagttca | 1260 |
| tccgtcatgg | aggccgccta | ctcgtgccac | tggtacgatg | gctccgagga | ggccaagacc | 1320 |
| ttcgtccaga | tcgtgtgcca | gcagtgccag | aaggcgatga | gcatatcggg | agcgaaattc | 1380 |
| ttcaccgtct | ccctggattt | gtttgcttcg | gttctgggtg | ccgtcgtcac | ctactttatg | 1440 |
| gtgctggtgc | agctcaagta | a | | | | 1461 |

<210> SEQ ID NO 6
<211> LENGTH: 486
<212> TYPE: PRT
<213> ORGANISM: Drosophila melanogaster

<400> SEQUENCE: 6

Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
            20                  25                  30

Asn Phe Thr Gly Gly Ser Ala Phe Met Lys Lys Val Tyr Ser Ser Val

-continued

```
                35                  40                  45
His Leu Val Phe Leu Leu Met Gln Phe Thr Phe Ile Leu Val Asn Met
 50                  55                  60

Ala Leu Asn Ala Glu Glu Val Asn Glu Leu Ser Gly Asn Thr Ile Thr
 65                  70                  75                  80

Thr Leu Phe Phe Thr His Cys Ile Thr Lys Phe Ile Tyr Leu Ala Val
                 85                  90                  95

Asn Gln Lys Asn Phe Tyr Arg Thr Leu Asn Ile Trp Asn Gln Val Asn
                100                 105                 110

Thr His Pro Leu Phe Ala Glu Ser Asp Ala Arg Tyr His Ser Ile Ala
                115                 120                 125

Leu Ala Lys Met Arg Lys Leu Phe Phe Leu Val Met Leu Thr Thr Val
                130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
                180                 185                 190

Met Phe Tyr Met Ile Ser Phe Ala Phe Gln Ile Tyr Tyr Val Leu Phe
                195                 200                 205

Ser Met Ile His Ser Asn Leu Cys Asp Val Met Phe Cys Ser Trp Leu
                210                 215                 220

Ile Phe Ala Cys Glu Gln Leu Gln His Leu Lys Gly Ile Met Lys Pro
225                 230                 235                 240

Leu Met Glu Leu Ser Ala Ser Leu Asp Thr Tyr Arg Pro Asn Ser Ala
                245                 250                 255

Ala Leu Phe Arg Ser Leu Ser Ala Asn Ser Lys Ser Glu Leu Ile His
                260                 265                 270

Asn Glu Glu Lys Asp Pro Gly Thr Asp Met Asp Met Ser Gly Ile Tyr
                275                 280                 285

Ser Ser Lys Ala Asp Trp Gly Ala Gln Phe Arg Ala Pro Ser Thr Leu
                290                 295                 300

Gln Ser Phe Gly Gly Asn Gly Gly Gly Asn Gly Leu Val Asn Gly
305                 310                 315                 320

Ala Asn Pro Asn Gly Leu Thr Lys Lys Gln Glu Met Met Val Arg Ser
                325                 330                 335

Ala Ile Lys Tyr Trp Val Glu Arg His Lys His Val Val Arg Leu Val
                340                 345                 350

Ala Ala Ile Gly Asp Thr Tyr Gly Ala Ala Leu Leu Leu His Met Leu
                355                 360                 365

Thr Ser Thr Ile Lys Leu Thr Leu Leu Ala Tyr Gln Ala Thr Lys Ile
                370                 375                 380

Asn Gly Val Asn Val Tyr Ala Phe Thr Val Val Gly Tyr Leu Gly Tyr
385                 390                 395                 400

Ala Leu Ala Gln Val Phe His Phe Cys Ile Phe Gly Asn Arg Leu Ile
                405                 410                 415

Glu Glu Ser Ser Ser Val Met Glu Ala Ala Tyr Ser Cys His Trp Tyr
                420                 425                 430

Asp Gly Ser Glu Glu Ala Lys Thr Phe Val Gln Ile Val Cys Gln Gln
                435                 440                 445

Cys Gln Lys Ala Met Ser Ile Ser Gly Ala Lys Phe Phe Thr Val Ser
                450                 455                 460
```

```
Leu Asp Leu Phe Ala Ser Val Leu Gly Ala Val Val Thr Tyr Phe Met
465                 470                 475                 480

Val Leu Val Gln Leu Lys
                485

<210> SEQ ID NO 7
<211> LENGTH: 39
<212> TYPE: DNA
<213> ORGANISM: Drosophila melanogaster

<400> SEQUENCE: 7
gccgaattcg ccaccatgcc atcggcagat cagatcctg                              39

<210> SEQ ID NO 8
<211> LENGTH: 34
<212> TYPE: DNA
<213> ORGANISM: Drosophila melanogaster

<400> SEQUENCE: 8
taatctagat caattcaggc ccagaagtcg cttg                                   34

<210> SEQ ID NO 9
<211> LENGTH: 34
<212> TYPE: DNA
<213> ORGANISM: Drosophila melanogaster

<400> SEQUENCE: 9
taagcggccg catgacaacc tcgatgcagc cgag                                   34

<210> SEQ ID NO 10
<211> LENGTH: 34
<212> TYPE: DNA
<213> ORGANISM: Drosophila melanogaster

<400> SEQUENCE: 10
ataccgcggc ttgagctgca ccagcaccat aaag                                   34

<210> SEQ ID NO 11
<211> LENGTH: 36
<212> TYPE: DNA
<213> ORGANISM: Drosophila melanogaster

<400> SEQUENCE: 11
taagcggccg catgacaatc gaggatatcg gcctgg                                 36

<210> SEQ ID NO 12
<211> LENGTH: 35
<212> TYPE: DNA
<213> ORGANISM: Drosophila melanogaster

<400> SEQUENCE: 12
ataccgcggt ttgccggtga cgccacgcag catgg                                  35
```